United States Patent [19]
Evers et al.

[11] 3,985,907
[45] Oct. 12, 1976

[54] NOVEL 3-FURYL BETA OXOALKYL SULFIDES, PROCESSES FOR PRODUCING SAME AND METHODS FOR USING SAME FOR ALTERING THE ORGANOLEPTIC PROPERTIES OF FOODSTUFFS

[75] Inventors: William J. Evers, Middletown; Howard H. Heinsohn, Jr., Hazlet; Manfred Hugo Vock, Locust; Christopher Giacino, Califon, all of N.J.

[73] Assignee: International Flavors & Fragrances Inc., New York, N.Y.

[22] Filed: May 29, 1975

[21] Appl. No.: 581,894

[52] U.S. Cl............................ 426/535; 260/347.2
[51] Int. Cl.[2]........................................ A23L 1/231
[58] Field of Search................... 260/347.2; 426/535

[56] References Cited
UNITED STATES PATENTS

| | | | |
|---|---|---|---|
| 3,666,495 | 5/1972 | Evers et al. | 426/535 |
| 3,872,111 | 3/1975 | Evers et al. | 260/347.2 |
| 3,873,731 | 3/1975 | Evers et al. | 426/535 |
| 3,891,710 | 6/1975 | Evers et al. | 260/347.2 |
| 3,910,966 | 10/1975 | Evers et al. | 260/347.2 |
| 3,917,869 | 11/1975 | Evers et al. | 426/535 |

*Primary Examiner*—Joseph M. Golian
*Attorney, Agent, or Firm*—Arthur L. Liberman; Harold Haidt

[57] ABSTRACT

3-Furyl beta-chalcogenalkyl sulfides having the structure:

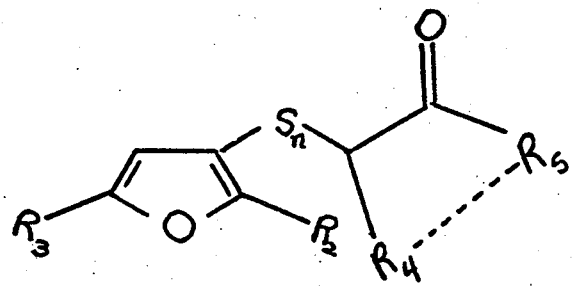

wherein $n$ is 1 or 2; $R_2$ and $R_3$ are each selected from the group consisting of methyl and hydrogen, at least one of $R_2$ and $R_3$ being methyl; and $R_4$ and $R_5$ taken separately, are each lower alkyl, or $R_4$ and $R_5$ taken together complete a cycloalkyl or bicycloalkyl group, such 3-furyl beta-oxoalkyl sulfides taken alone or in admixture being useful in altering or modifying or enhancing the organoleptic properties of foodstuffs, and processes for preparing these 3-furyl beta-oxalkyl sulfides where $n$ is 1 using the reaction:

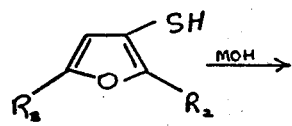

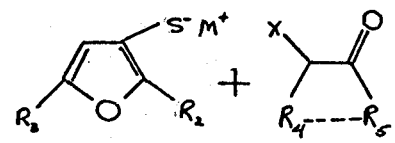

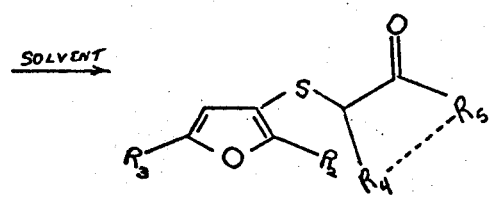

wherein X is halogen selected from the group consisting of chlorine and bromine; wherein M is alkali metal and $R_2$, $R_3$, $R_4$ and $R_5$ are each defined as above.

27 Claims, 15 Drawing Figures

EXAMPLE V
THIN LAYER CHROMATOGRAPHY PLATE OF FRACTIONS 3-21

NMR SPECTRUM FOR THE PRODUCT OF EXAMPLE III

I.R. SPECTRUM FOR THE PRODUCT OF EXAMPLE III

NMR SPECTRUM FOR THE PRODUCT OF EXAMPLE V

I.R. SPECTRUM FOR THE PRODUCT OF EXAMPLE V

I.R SPECTRUM FOR THE PRODUCT OF EXAMPLE VII

NMR SPECTRUM FOR THE PRODUCT OF EXAMPLE IX

I.R. SPECTRUM FOR THE PRODUCT OF EXAMPLE IX

I.R. SPECTRUM FOR THE PRODUCT OF EXAMPLE XI

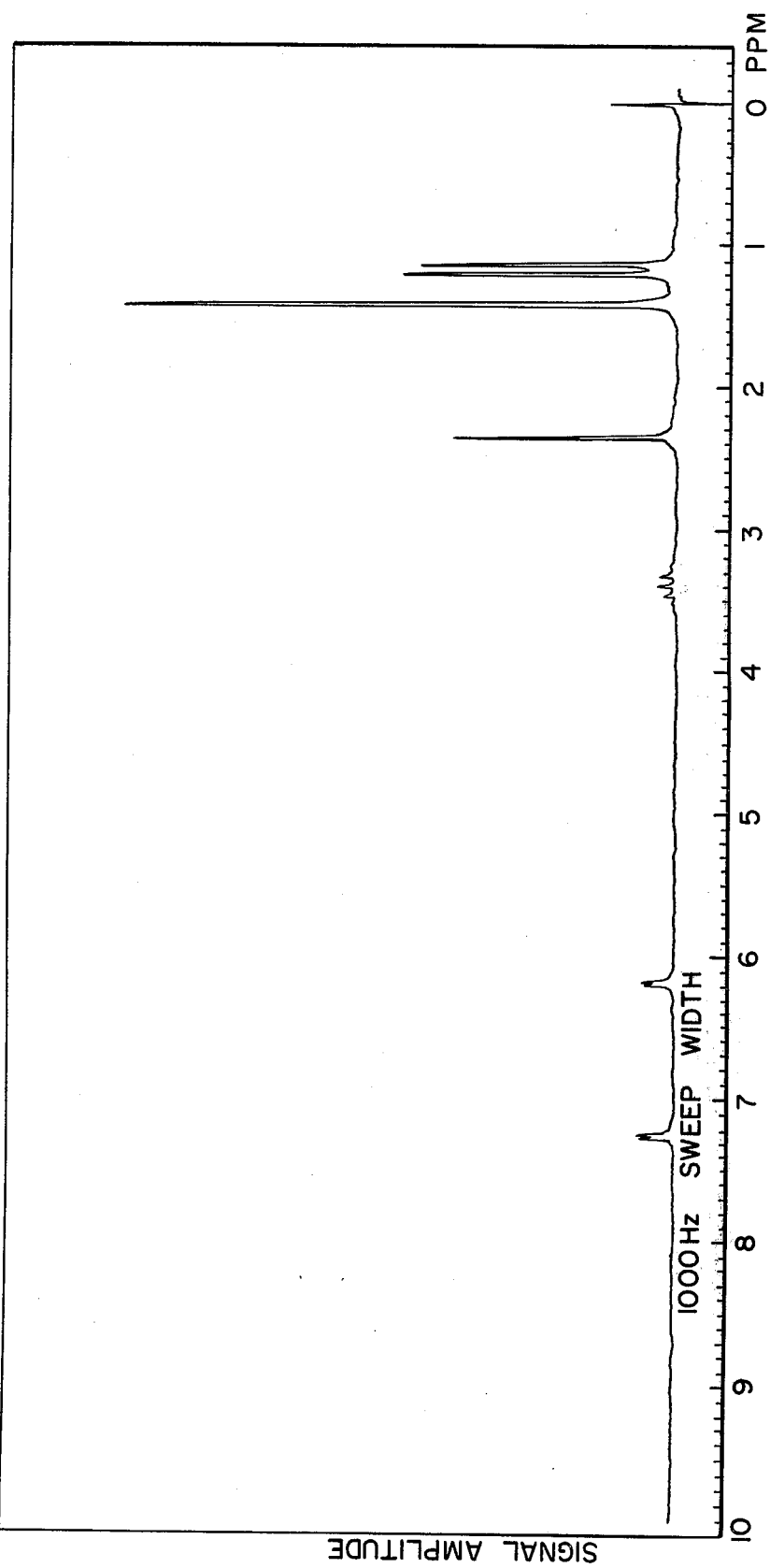

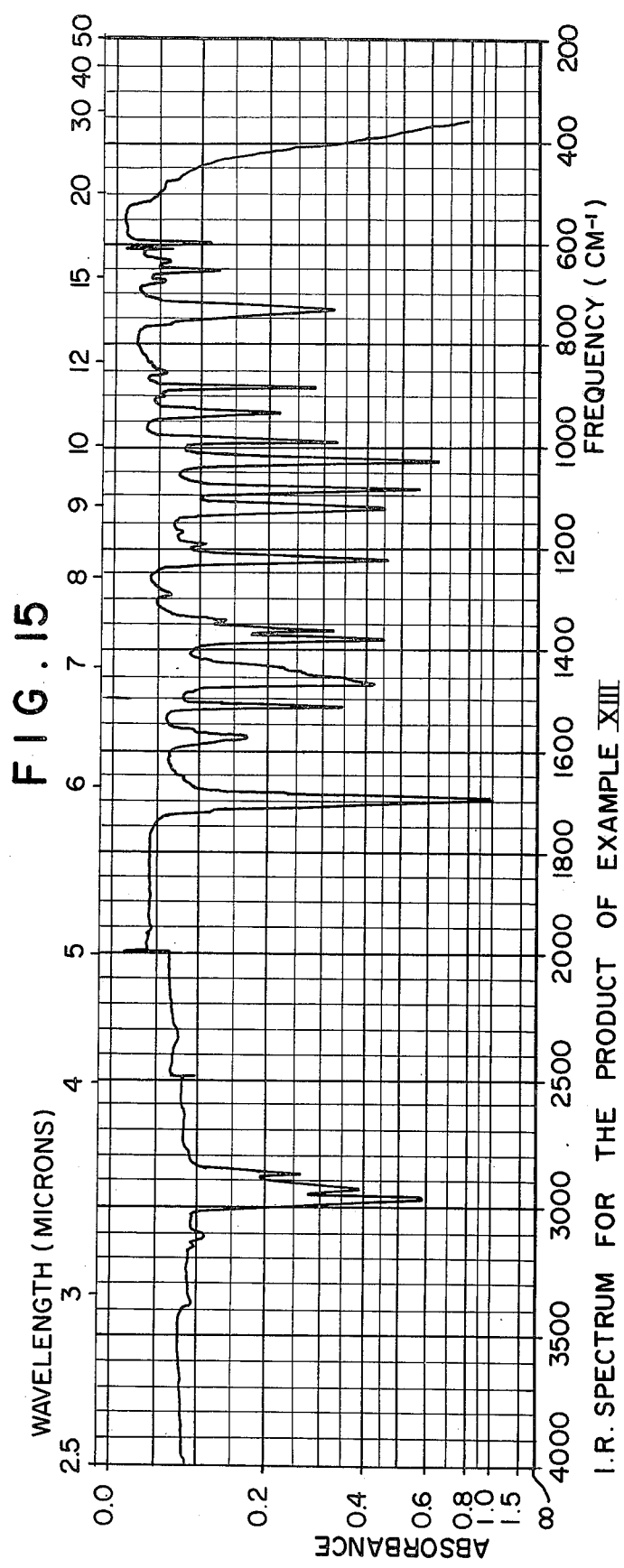

NOVEL 3-FURYL BETA OXOALKYL SULFIDES, PROCESSES FOR PRODUCING SAME AND METHODS FOR USING SAME FOR ALTERING THE ORGANOLEPTIC PROPERTIES OF FOODSTUFFS

BACKGROUND OF THE INVENTION

The present invention relates to novel 3-furyl betaoxoalkyl sulfides.

Artificial flavoring agents for foodstuffs have received increasing attention in recent years. In many areas, such food flavoring agents are preferred over natural flavoring agents at least in part because of the uniform flavor that may be so obtained. For example, natural food flavoring agents such as extracts, essences, concentrates and the like are often subject to wide variation due to changes in the quality, type and treatment of the raw materials. Such variation can be reflected in the end product and results in unreliable flavor characteristics and uncertainty as to consumer acceptance and cost. Additionally, the presence of the natural product in the ultimate food may be undesirable because of increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artificial flavoring agents is that of achieving as nearly as possible a true flavor reproduction. This generally proves to be a difficult task since the mechanism for flavoring development in many foods is not understood. This is notable in products having sweet, meaty and roasted meat flavor and nut-like flavor characertistics. It is also notable in products having vegetable-like and hydrolyzed vegetable protein-like and anise-like flavor characteristics.

Reproduction of roasted, beef brothy, nutty and sweet, meaty flavors and aromas and hydrolyzed vegetable protein-like flavors and aromas has been the subject of the long and continuing search by those engaged in the production of foodstuffs. The severe shortage of foods, especially protein foods, in many parts of the world has given rise to the need for utilizing non-meat sources of proteins and making such proteins as palatable and as meat-like as possible. Hence, materials which will closely simulate or exactly reproduce the flavor and aroma of roasted meat and sweet, meat products, vegetable products and products having nut-like taste are required.

Moreover, there are a great many meat containing or meat based foods presently distributed in a preserved form. Examples being condensed soups, dry-soup mixes, dry meat, freeze-dried or lyophilized meats, packaged gravies and the like. While these products contain meat or meat extracts, the fragrance, taste and other organoleptic factors are very often impaired by the processing operation and it is desirable to supplement or enhance the flavors of these preserved foods with versatile materials which have either roasted meat or sweet meat or vegatable-like or nut-like nuances.

U.S. Pat. No. 3,666,495 provided materials having such desirable meat, roast meat and roasted fragrance and flavor notes. Such materials are organic oxygen containing heterocyclics wherein the second carbon atom from the oxygen atom contains a sulfur substituent and included 3-thia furan compounds having the structure:

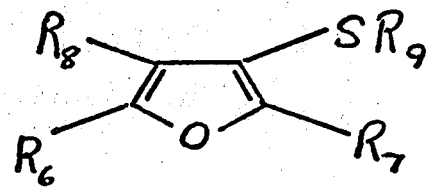

wherein $R_6$, $R_7$, $R_8$ and $R_9$ are the same or different alkyl or hydrogen. The process disclosed in this patent indicated that such furan 3-thiols and alkyl substituted furan 3-thiols can be produced by the reaction of an appropriate dihydrofuranone-3 or tetrahydrofuranone-3 with hydrogen sulfide in the presence of anhydrous hydrogen chloride at temperatures of −60° C to −100° C.

Nothing in the prior art, however, sets forth implicitly or explicitly the 3-furyl beta -oxoalkyl, sulfides of our invention and their unique and advantageous and unobvious flavor properties.

U.S. Application for Ser. No. 542,830, filed on Jan. 21, 1975, discloses the use in meat flavors of 3-furyl beta chalcogen sulfides having the structure:

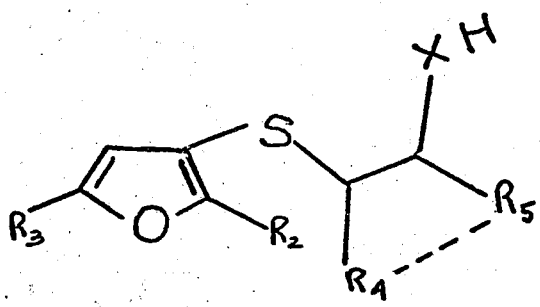

where X is a chalcogen selected from the group consisting of oxygen and sulfur; $R_2$ and $R_3$ are each selected from the group consisting of methyl and hydrogen, at least one of $R_2$ and $R_3$ being methyl; and $R_4$ and $R_5$, taken separately, are each methyl, or $R_4$ and $R_5$ taken together are tetramethylene.

The present invention provides novel 3-furyl betaoxoalkyl sulfides useful for altering the organoleptic properties of foodstuffs, a novel process for producing said 3-furyl betaoxoalkyl sulfides as well as methods for altering or enhancing or modifying the organoleptic properties, e.g. taste and aroma, of said foodstuffs.

The novel compounds of our invention are 3-furyl beta-oxoalkyl sulfides having the structure:

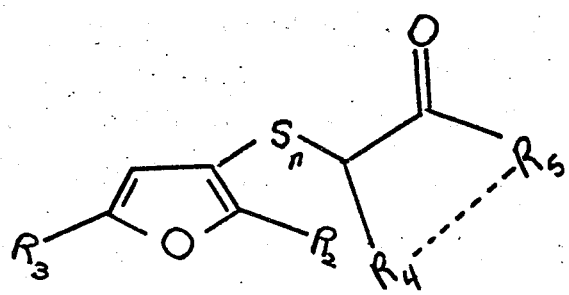

wherein n is 1 or 2 and wherein $R_2$ and $R_3$ are each selected from the group consisting of methyl and hydrogen, at least one of $R_2$ and $R_3$ being methyl and $R_4$ and $R_5$ taken separately, are each lower alkyl, or $R_4$ and $R_5$ taken together form a cycloalkyl ring or bi-cycloalkyl ring.

Thus, the 3-furyl beta-oxoalkyl sulfides contemplated within the scope of our invention are, for example:

| 3-Furyl-beta-Oxoalkyl Sulfide Compound | Structure |
|---|---|
| (1,3-diethylacetonyl)(2-methyl-3-furyl)sulfide | 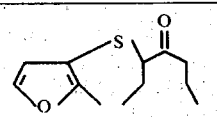 |
| (2-methyl-3-furyl)(3,3,3-trimethyl-acetonyl)sulfide | 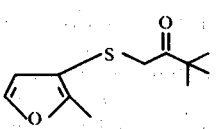 |
| (2-methyl-3-furyl)(1-methyl-2-oxopropyl)disulfide | 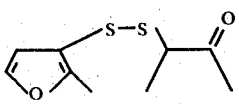 |
| (2-methyl-3-furyl)(1-methyl-2-oxopropyl)sulfide | 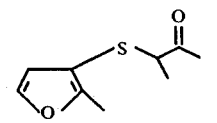 |
| (1,3-diethylacetonyl)(2,5-dimethyl-3-furyl)sulfide | 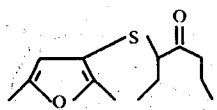 |
| (Camphor-3-yl)(2-methyl-3-furyl)sulfide | 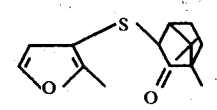 |
| (2-methyl-3-furyl)(1,1,3,3-tetramethylacetonyl)sulfide | 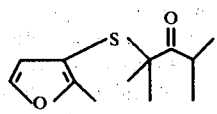 |

A number of the 3-furyl beta-oxoalkyl sulfides of our invention (where n=1) may be produced according to a process which comprises the steps of:

i. Carrying out a reaction of a 3-mercapto furan with an oxo-α-haloalkane, cycloalkane or bicycloalkane (alternatively named: alpha-haloalkanone, cycloalkanone or bicycloalkanone) to form the compounds of our invention according to the following reaction:

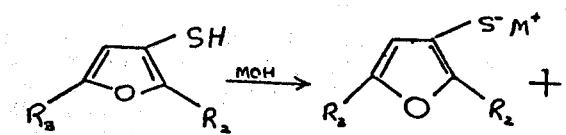

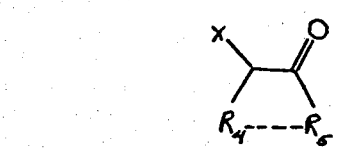

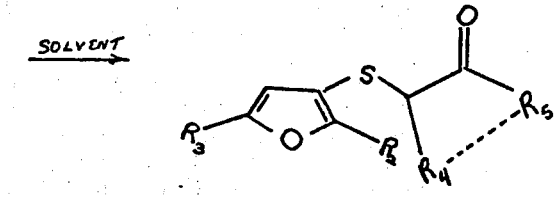

ii. Physically separating said 3-furyl beta-oxoalkyl sulfides from the reaction mass;

wherein X is a halogen selected from the group consisting of chlorine and bromine; wherein $R_2$, $R_3$, $R_4$ and $R_5$ are defined as above, and wherein M is an alkali metal.

The following table sets forth examples of specific reactants and the resulting products produced using the process of our invention:

TABLE I

| Oxo-alpha-halo alkane or cycloalkane or bicycloalkane reactant | 3-furan-thiol reactant | 3-Furyl-beta-Oxoalkyl Sulfide Compound | Structure |
|---|---|---|---|
| 3-chloro-4-heptanone | 2-methyl-3-furan thiol | (1,3-diethylacetonyl)(2-methyl-3-furyl)sulfide | 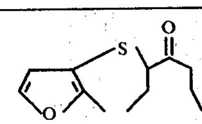 |
| 1-chloro-3,3-dimethyl butan-2-one | 2-methyl-3-furan thiol | (2-methyl-3-furyl)(3,3,3-trimethyl-acetonyl)sulfide | 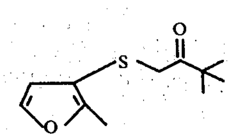 |
| 3-chloro-butan-2-one | 2-methyl-3-furan thiol | (2-methyl-3-furyl)(1-methyl-2-oxopropyl)sulfide | 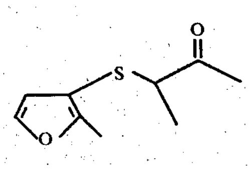 |

TABLE I-continued

| Oxo-alpha-halo alkane or cycloalkane or bicyclo-alkane reactant | 3-furan-thiol reactant | 3-Furyl-beta-Oxoalkyl Sulfide Compound | Structure |
|---|---|---|---|
| 3-chloro-heptan-4-one | 2,5-dimethyl-3-furan thiol | (1,3-diethylacetonyl)(2,5-dimethyl-3-furyl)sulfide | 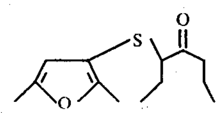 |
| Camphor-3-yl bromide | 2-methyl-3-furan thiol | (Camphor-3-yl)(2-methyl-3-furyl)sulfide | 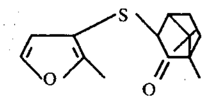 |
| 2-chloro-2,4-dimethyl-pentan-3-one | 2-methyl-3-furan thiol | (2-methyl-3-furyl)(1,1,3,3-tetramethylacetonyl)sulfide | 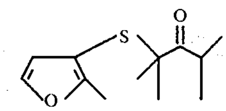 |

The reaction of our invention, in order to proceed in a practical manner, takes place using an alkali metal salt of a 3-furan thiol, such as the sodium or potassium salt of 2-methyl-3-furan thiol or the sodium or potassium salt of 2,5-dimethyl-3-furan thiol. The alpha haloalkanone or cycloalkanone or bicycloalkanone may be a bromo derivative or a chloro derivative. Each of the reactants is preferably dissolved in an appropriate reaction solvent, e.g. methanol.

Other solvents, which may be used in carrying out this reaction, are ethanol or isopropanol.

The mole ratio of the reactants, the alkali metal salt of the 3-furan thiol: alpha haloalkanone or cycloalkanone or bicycloalkanone may vary from 1:1 up to 5:1, with a preferred ratio of alkali metal salt of 3-furan thiol: alpha haloalkanone or bicycloalkanone or cycloalkanone of 1:1.

The reaction temperature may vary from about 10° C up to about 100° C. The time of reaction is a function of the reaction temperature with lower reaction temperatures giving rise to longer periods of time of reaction and higher temperatures of reaction giving rise to much shorter periods of time of reaction.

The reaction is preferably carried out at atmospheric pressure, but pressures greater than atmospheric, e.g. 5 atmospheres may be used without detrimentally affecting the yield of product or the time of reaction which is required to obtain such yield.

At the end of the reaction, the reaction product is extracted from the reaction mass using a non-reactive solvent, e.g. n-hexane or methylene dichloride, after the reaction mass is first quenched with water and neutralized with aqueous acid. The solvent extract is then dried, concentrated and distilled preferably by means of vacuum distillation.

A process for preparing the disulfides of our invention involves reacting a 2-alkyl-3-furan thiol with an oxoalkyl or oxocycloalkyl alpha thiol and iodine in the presence of nonreactive solvent e.g., diethyl ether. Thus, for example, (i) 1-mercapto-2-oxo-3-methyl butane is reacted with iodine (as the oxidizing agent) and 2,5-dimethyl-3-furan thiol, thereby forming (2-oxo-3-methyl butyl) (2,5-dimethyl-3-furyl) disulfide; and (ii) 2-oxo-cyclohexylmercaptan is reacted with iodine and 2-methyl-3-furan thiol to form (2-oxocyclohexyl) (2-methyl-3-furyl) disulfide. This reaction takes place in the presence of a base, e.g., an alkali metal carbonate such as sodium carbonate. The mole ratio of $I_2$:base:2-alkyl-3-furan thiol:oxoalkyl alpha mercaptan is preferably about 0.75:0.75:0.50:1.0. The reaction may be carried out at temperatures in the range of 10° C up to 35° C with room temperature being most convenient.

The 3-furyl beta-oxoalkyl sulfides of our invention, produced as stated above have useful organoleptic properties giving rise to the use as foodstuff flavors or flavor adjuvants or flavor enhancers as set forth in an illustrative manner in the following table:

TABLE II

| 3-Furyl-beta-Oxoalkyl Sulfide Compound | Structure | Flavor Properties |
|---|---|---|
| (1,3-diethylacetonyl)(2-methyl-3-furyl) sulfide | 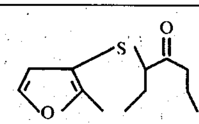 | Hydrolysed vegetable protein-like, meaty, beefy broth aroma and sweet, hydrolyzed vegetable protein-like, meaty flavors with beef broth and pot roast nuances. |
| (2-methyl-3-furyl)(3,3,3-trimethyl-acetonyl)sulfide | 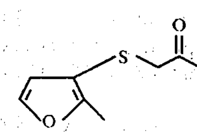 | Hydrolyzed vegetable protein-like, meaty, beef broth-like aroma and flavor with an astringent nuance, and in addition, green herbaceous and minty notes. |

TABLE II-continued

| 3-Furyl-beta-Oxoalkyl Sulfide Compound | Structure | Flavor Properties |
|---|---|---|
| (2-methyl-3-furyl)(1-methyl-2-oxopropyl)disulfide | 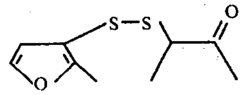 | Meaty, sweet, yeasty aroma and flavor with hydrolyzed vegetable protein-like and nutty nuances. |
| (2-methyl-3-furyl)(1-methyl-2-oxopropyl)sulfide | 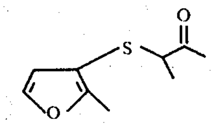 | Sweet, meaty, rubbery aroma with a cooked liver nuance and a sweet, cooked liver, hydrolyzed vegetable protein-like flavor with rubbery, meaty, pecan, and mouth feel nuances. |
| (1,3-diethylacetonyl)(2,5-dimethyl-3-furyl)sulfide | 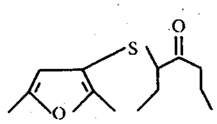 | Meaty, sweet and metallic aroma with a bloody nuance and a meaty, sweet and metallic flavor with hydrolyzed vegetable protein-like and bloody nuances. |
| (Camphor-3-yl)(2-methyl-3-furyl)sulfide | 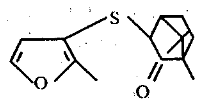 | Sweet, meaty, crispy aroma and a sweet, roasted flavor. |
| (2-methyl-3-furyl)(1,1,3,3-tetramethylacetonyl)sulfide | 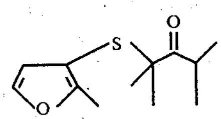 | Meaty, sulfury aroma, meaty, roast onion and sulfury flavor with a green note. It also has a garlic and alliaceous nuance |

Thus, the 3-furyl beta-oxoalkyl sulfides produced according to the instant invention can be used to alter, vary, fortify, modify, enhance or otherwise improve the organoleptic properties, including flavor and/or aroma, of a wide variety of materials which are ingested, consumed, or otherwise organoleptically sensed.

The term "alter" in its various forms will be understood herein to mean the supplying or imparting a flavor character or note to an otherwise bland, relatively tasteless substance, or augmenting an existing flavor characteristic where the natural flavor is deficient in some regard, or supplementing the existing flavor or aroma impression to modify the organoleptic character. The materials which are so altered are generally referred to herein as consumable materials.

Such 3-furyl beta-oxoalkyl sulfides are accordingly useful in flavoring compositions. Flavoring compositions are hereintaken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt and other alcoholic or non-alcoholic beverages, milk and dairy products, nut butters such as peanut butter and other spreads, seafoods including fish, crustaceans, mollusks and the like, candies, breakfast foods, baked goods, vegetables, cereals, soft drinks, snack foods, dog and cat foods, other veterinary products, and the like.

When the 3-furyl beta-oxoalkyl sulfides according to this invention are used in a food flavoring composition, they can be combined with conventional flavoring materials or adjuvants. Such co-ingredients or flavoring adjuvants are well known in the art for such use and have been extensively described in the literature. Apart from the requirement that any such adjuvant material is ingestibly acceptable, and thus non-toxic or otherwise non-deleterious, conventional materials can be used and broadly include other flavor materials, vehicles, stabilizers, thickeners, surface active agents, conditioners and flavor intensifiers.

Examples of preferred co-flavoring adjuvants are:
Methyl thiazole alcohol (4-methyl-5-beta-hydroxyethyl thiazole);
2-Methyl butanethiol;
4-Mercapto-2-butanone;
3-Mercapto-2-pentanone;
1-Mercapto-2-propanone;
Benzaldehyde;
Furfural;
Furfural alcohol;
2-Mercapto propionic acid;
Alkyl pyrazine;
Methyl pyrazine;
2-Ethyl-3-methyl pyrazine;
Tetramethyl pyrazine;
Polysulfides;
Dipropyl disulfide;
Methyl benzyl disulfide;
Alkyl thiophenes;
2-Butyl thiophene;
2,3-Dimethyl thiophene;
5-Methyl furfural;
Acetyl furan;
2,4-Decadienal;
Guiacol;
Phenyl acetaldehyde;
δ-Decalactone;

d-Limonene;
Acetoin;
Amyl acetate;
Maltol;
Ethyl butyrate;
Levulinic acid;
Piperonal;
Ethyl acetate;
n-Octanal;
n-Pentanal;
Hexanal;
Diacetyl;
Monosodium glutamate;
Sulfur-containing amino acids;
Cysteine;
Hydrolyzed vegetable protein;
2-Methylfuran-3-thiol;
2-Methyldihydrofuran-3-thiol;
2,5-dimethylfuran-3-thiol;
Hydrolyzed fish protein; and
Tetramethyl pyrazine The 3-furyl beta-oxoalkyl sulfides or the compositions incorporating them, as mentioned above, can be combined with one or more vehicles or carriers for adding them to the particular product. Vehicles can be edible or otherwise suitable materials such as ethyl alcohol, propylene glycol, water and the like. Carriers include materials such as gum arabic, carrageenan, other gums and the like. The 3-furyl beta-oxoalkyl sulfides according to this invention can be incorporated with the carriers by conventional means such as spray-drying, drum-drying and the like. Such carriers can also include materials for coacervating the 3-furyl beta-oxoalkyl sulfides (and other flavoring ingredients, as present) to provide encapsulated products. When the carrier is an emulsion the flavoring composition can also contain emulsifiers such as mono- and diglycerides or fatty acids and the like. With these carriers or vehicles, the desired physical form of the composition can be prepared.

The quantity of 3-furyl beta-oxoalkyl sulfides utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage; if any, to which the product will be subjected; and the preconsumption treatment, such as baking, frying, and so on, given to the product by the ultimate consumer. Accordingly, the terminology "effect amount" and "sufficient amount" is understood in the context of the present invention to be quantitatively adequate to alter the flavor of the foodstuff.

It is accordingly preferred that the ultimate composition contain from about 0.005 parts per million (ppm) to about 250 ppm of 3-furyl beta-oxoalkyl sulfides or mixtures thereof. More particularly, in food compositions it is desirable to use from about 0.01 ppm to 100 ppm for enhancing flavors and in certain preferred embodiments of the invention, from about 0.01 to 50 ppm of the derivatives are included to add positive flavors to the finished product.

The amount of 3-furyl beta-oxoalkyl sulfides or mixtures thereof of our invention to be utilized in flavoring compositions can be varied over a wide range depending upon the particular quality to be added to the foodstuff. Thus, amounts of one or more derivatives according to the present invention of from about 0.5 ppm up to 80 or 90 percent of the total flavoring composition can be incorporated in such compositions. It is generally found to be desirable to include from about 1 ppm up to about 0.1 percent of the 3-furyl beta-oxoalkyl sulfides in such compositions.

The following examples are given to illustrate embodiment of the invention as it is preferred to practice it. It will be understood that these examples are illustrative and the invention is not to be considered as restrictive thereto except as indicated in the appended claims.

All parts, proportions, percentages, and ratios here are by weight unless otherwise indicated.

EXAMPLE I

PREPARATION OF
(1,3-DIETHYLACETONYL)(2-METHYL-3-FURYL)SULFIDE

Part A
Reaction:

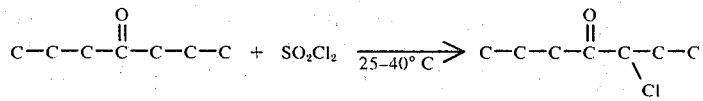

Into a 250 ml 3 neck round bottom flask equipped with magnetic stirrer, 50 ml addition funnel, pot thermometer and reflux condenser (with vacuum outlet to water aspirator) and cold water bath, 71 g (0.62 moles) of di-propyl ketone is placed. Over a period of 1 hour with external cooling being applied, 12 ml (20.3 g; 0.15 moles) of $SO_2Cl_2$ is added while removing the acidic gases, hydrogen chloride and sulfur dioxide, using the water aspirator. After the 1 hour period, vacuum is applied with stirring continuing for another 1½ hours. The reaction mass is then transferred to a 250 ml one neck round bottom flask to which vacuum is applied using a water aspirator at room temperature. The resulting crude oil weighing 75.0 g is then removed from the flask for distillation. The 3-chloro-4-heptanone reaction product is then distilled at a vacuum of 206 mm Hg; a vapor temperature of 113° – 120° C and a pot temperature of 132° – 140° C. The structure of the product is confirmed by MS, IR and NMR analyses.

Part B
Reaction:

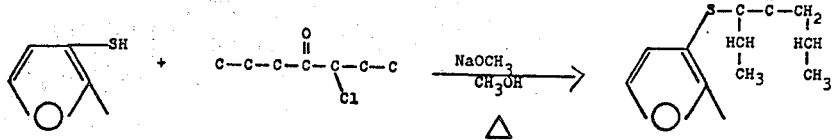

Into a 25 ml round bottom 3 neck flask equipped with magnetic stirrer, Y-tube, nitrogen inlet tube, reflux condenser (equipped with calcium chloride drying tube), thermometer and heating mantle the following materials are placed:
i. 2-methyl-3-furan thiol 0.57 g (0.005 moles) in absolute methanol (3 ml);
ii. solution of sodium methoxide 0.27 g (0.005 moles) in methanol (3 ml).

The solution is stirred under dry nitrogen at 25°–30°C for 10 minutes. A solution of 0.74 g (0.005 moles) of 3-chloro-4-heptanone (prepared in Part A) in 1 ml absolute methanol is then slowly added to the reaction mass with stirring. The reaction mass is then heated at reflux for a period of 1 hour, after which it is cooled to room temperature and is treated with 10 ml of water. The reaction mass is then neutralized to a pH of 5–6 with 10% hydrochloric acid and 5 ml hexane is added with stirring. The reaction mass is then transferred to a separatory funnel and the organic and aqueous phases are separated. The aqueous phase is diluted with 5 ml water and extracted with 7 ml n-hexane. The hexane extracts are combined with the organic phase which is then washed with 5 ml saturated sodium chloride and then dried over anhydrous sodium sulfate and gravity-filtered. The resulting material is concentrated using a rotary evaporator under water-aspirator vacuum. The product is isolated by GLC trapping; (8 feet × ¼ inch SE-30 column) and NMR, IR and Mass Spectral analyses confirm that the compound has the structure:

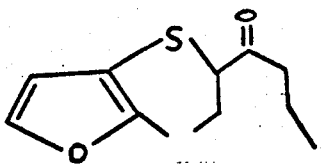

This material has a hydrolyzed vegetable protein-like, meaty, beefy broth aroma and sweet, hydrolyzed vegetable proteinlike, meaty flavors with beef broth and pot roast nuances.

NMR analysis is as follows:

| SIGNAL | | INTERPRETATION | |
|---|---|---|---|
| 0.94 ppm | (t) | $CH_3-C-C-\overset{\overset{O}{\|\|}}{C}$ | |
| 0.98 | (t) | $CH_3-C-C-S-$ | 6 H |
| 1.92–1.44 | (m) | $-CH_2-$ | 4 H |
| 2.32 | (s) | Furan methyl proton | 3 H |
| 2.60 | (m) | $-CH_2-\overset{\overset{\|\|}{O}}{C}-$ | 2 H |
| 3.24 | (t) | $-S-\overset{\overset{O}{\|\|}}{\underset{H}{C}}-C-$ | 1 H |
| 6.24 | (d) | $H_4$ of Furan | 1 H |
| 7.26 | (d) | $H_3$ of Furan | 1 H |

Ir analysis is as follows:
725, 880, 1085, 1120, 1220, 1380, 1450, 1510, 1700, 2870, 2930, 2960 cm$^{-1}$.

Mass Spectral analysis is as follows:

| m/e | Relative Intensity |
|---|---|
| 27 | 13[6] |
| 39 | 9 |
| 41 | 18[5] |
| 43 | 36[3] |
| 45 | 10 |
| 71 | 12 |
| 113 | 100[1] |
| 114 | 9 |
| 155 | 66[2] |
| M226 | 35[4] |

EXAMPLE II

The (1,3-diethylacetonyl)(2-methyl-3-furyl) sulfide prepared in Example I is dissolved in propylene glycol to provide a 0.1% solution. This solution in the amount of 0.9 g is added to 7.3 g of a soup base consisting of:

| Ingredient | Parts by Weight |
|---|---|
| Fine ground sodium chloride | 35.5 |
| Hydrolyzed vegetable protein | 27.5 |
| Monosodium glutamate | 18.0 |
| Sucrose | 11.0 |
| Beef fat | 5.5 |
| Sethness caramel color (powder B & C) | 2.7 |

The resulting mixture has a hydrolyzed vegetable protein-like, beefy aroma and sweet, hydrolyzed vegetable protein-like, meaty flavor with intensified natural beef broth and pot roast nuances.

EXAMPLE III

PREPARATION OF (2-METHYL-3-FURYL)(3,3,3-TRIMETHYLACETONYL) SULFIDE

Reactions

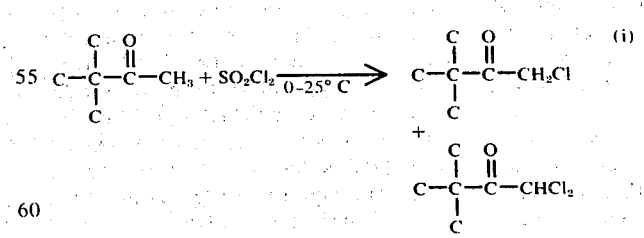

Reaction:

(ii)

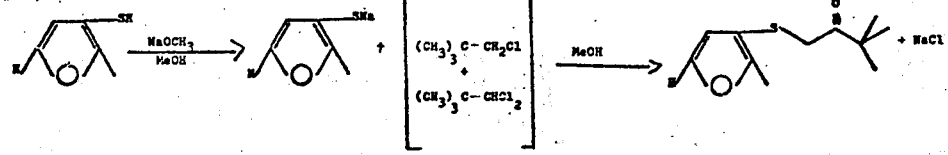

Into a 25 ml round bottom flask equipped with magnetic stirrer, and dry ice-acetone bath is placed 3.0 g (0.03 moles) of pinacolone (t-butyl methyl ketone). The pinacolone is cooled to 0° C and 2.0 ml (0.075 moles) of sulfuryl chloride ($SO_2Cl_2$) is added slowly. The reaction is exothermic, evolving hydrogen chloride and sulfur dioxide. These acidic gases are removed using water-aspirator vacuum. The reaction mass is then washed with 1 ml saturated sodium bicarbonate and dried over anhydrous sodium sulfate and filtered, yielding a crude oil weighing 1.7 g.

GLC analysis (SE-30 column) and trapping; and IR, NMR and MS analyses show that the resulting material is a mixture of:

i. 32% by weight of 1-chloro-t-butylmethyl-ketone having the structure:

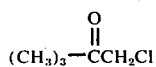

ii. 41% 1,1-dichloro-t-butyl-methyl ketone having the structure:

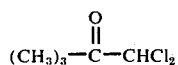

0.75 g of this material is then intimately admixed with 0.005 moles of 2-methyl-3-furan thiol and 0.005 moles sodium methylate in 6 ml anhydrous methanol. The reaction mass is stirred for a period of 2½ hours at a temperature of from 25° C up to 35° C with external cooling being applied due to the fact that the reaction is exothermic. At the end of the 2½ hour period the reaction mixture is worked up as in Example I and a crude amber oil weighing 0.78 g is recovered. The product ia isolated by GLC trapping and Mass Spectral, NMR and IR analyses confirm that this material is a compound having the structure:

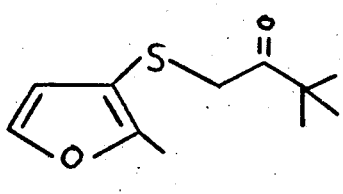

This material has a hydrolyzed vegetable protein-like, meaty and beef broth-like aroma and flavor with an astringent nuance, and, in addition, green herbaceous and minty notes.

NMR analysis is as follows:

| SIGNAL | | INTERPRETATION | |
|---|---|---|---|
| 1.16 ppm | (s) | $CH_3$<br>\|<br>$CH_3-C-C=O$<br>\| \|<br>$CH_3$ | 9 H |
| 2.36 | (s) | Furyl methyl protons | 3 H |
| 3.64 | (s) | O<br>\|\|<br>$-S-CH_2-C-$ | 2 H |
| 6.38 | (d) | $H_4$ of Furan | 1 H |
| 7.37 | (d) | $H_5$ of Furan | 1 H |

IR analysis is as follows: 725, 880, 995, 1050, 1080, 1120, 1215, 1360, 1380, 1460, 1470, 1510, 1700, 2910, 2960, cm$^{-1}$.

Mass Spectral analysis is as follows:

| m/e | Relative Intensity |
|---|---|
| 29 | 10⁶ |
| 39 | 6 |
| 41 | 14⁴ |
| 43 | 11⁵ |
| 45 | 7 |
| 57 | 100¹ |
| 113 | 10 |
| 127 | 24³ |
| 128 | 6 |
| M212 | 33² |

EXAMPLE IV

The (2-methyl-3-furyl)(3,3,3-trimethylacetonyl) sulfide prepared in Example III is dissolved in propylene glycol to provide a 0.1% solution. This solution in the amount of 0.9 g is added to 7.3 g of a soup base consisting of:

| Ingredient | Parts by Weight |
|---|---|
| Fine ground sodium chloride | 35.5 |
| Hydrolyzed vegetable protein | 27.5 |
| Monosodium glutamate | 18.0 |
| Sucrose | 11.0 |
| Beef fat | 5.5 |
| Sethness caramel color (powder B & C) | 2.7 |

The resulting mixture has a hydrolyzed vegetable protein-like meaty, beef broth-like aroma and flavor with an astringent nuance, and in addition, green herbaceous minty notes.

EXAMPLE V

PREPARATION OF
(2-METHYL-3-FURYL)(1-METHYL-2-OXOPROPYL) DISULFIDE

Reaction:

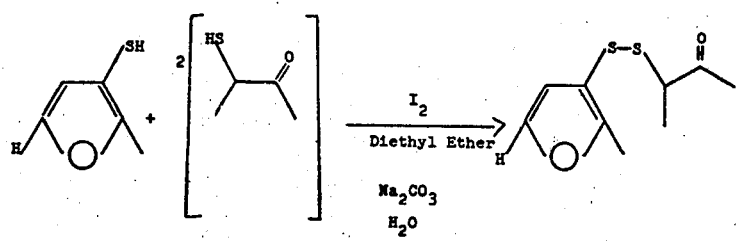

0.005 moles of 2-methyl-3-furan thiol is admixed with 1.04 grams (0.01 moles) of 3-mercapto-2-butanone and the resulting mixture is dissolved in 12 ml of diethylether. Sodium carbonate (0.8 grams; 0.0075 moles) dissolved in 8 ml of water is added, with stirring, to the resulting mixture. Iodine (1.9 grams; 0.0075 moles) dissolved in 6 ml diethylether is added dropwise until the iodine color remains. The reaction mass is stirred for a period of 30 minutes at room temperature. The reaction mixture is then placed in a separatory funnel and the aqueous layer is separated from the ether layer. The ether layer is then washed with 5 ml of saturated sodium bicarbonate solution, followed by 4 ml of 0.05 m sodium thiosulfate. The washed material is then filtered through anhydrous sodium sulfate and concentrated to a crude oil weighing 1.30 grams. GLC analysis indicates 3 overlapping peaks which could not be separated by GLC trapping (Conditions: SE-30 column programmed at 130° C and 6° C/minute). Peak 2 is then separated from peaks 1 and 3 using column chromatography as follows:

1.2 grams of the reaction product (crude) is dissolved in 3 ml n-hexane. This material is then placed in a 4.4 × 60 cm chromatography column packed with 48 grams of silicic acid (40:1 weight ratio). The following fractions are eluted from the column using solutions of n-hexane or diethylether in n-hexane.

| Fraction No. | Solvent | Volume of Solvent | Weight Recovered |
|---|---|---|---|
| 1 | 100% hexane | 100 ml | — |
| 2 | 100% hexane | 100 ml | — |
| 3 | 100% hexane | 90 ml | 0.05 g |
| 4 | 100% hexane | 55 ml | 0.025 g |
| 5 | 100% hexane | 60 ml | 0.025 g |
| 6 | 100% hexane | 70 ml | 0.02 g |
| 7 | 100% hexane | 70 ml | 0.01 g |
| 8 | 1% diethylether in n-hexane | 70 ml | 0.01 g |
| 9 | 1% diethylether in n-hexane | 75 ml | 0.01 g |
| 10 | 1% diethylether in n-hexane | 75 ml | — |
| 11 | 1% diethylether in n-hexane | 75 ml | — |
| 12 | 1% diethylether in n-hexane | 75 ml | — |
| 13 | 1% diethylether in n-hexane | 75 ml | 0.01 g |
| 14 | 1% diethylether in n-hexane | 75 ml | 0.02 g |
| 15 | 1% diethylether in n-hexane | 75 ml | 0.02 g |
| 16 | 1% diethylether in n-hexane | 75 ml | 0.02 g |
| 17 | 1% diethylether in n-hexane | 75 ml | 0.04 g |
| 18 | 1% diethylether in n-hexane | 80 ml | 0.02 g |
| 19 | 1% diethylether in n-hexane | 80 ml | 0.02 g |
| 20 | 1% diethylether in n-hexane | 75 ml | 0.01 g |
| 21 | 1% diethylether in n-hexane | 75 ml | 0.01 g |
| 22 | 1% diethylether | 75 ml | NOT RECORDED |
| 23 | 1% diethylether in n-hexane | 70 ml | |
| 24 | 1% diethylether in n-hexane | 75 ml | |
| 25 | 1% diethylether in n-hexane | 75 ml | |
| 26 | 1% diethylether in n-hexane | 75 ml | |
| 27 | 1% diethylether in n-hexane | 75 ml | |
| 28 | 1% diethylether in n-hexane | 75 ml | |
| 29 | 1% diethylether in n-hexane | 75 ml | |
| 30 | 1% diethylether in n-hexane | 75 ml | |

Fractions 3, 5, 8, 12, 13, 14, 15, 16, 17, 18, 19, 20, 21, 22, 23, 25, 26, 27, 28, 29 and 30 were then analyzed using thin layer chromatography (TLC). Conditions: Pre-coated TLC plates obtained from EM Reagents Co. - of Elmsford, N.Y. coated with Silica Gel and developed wit a 20% solution of diethyl ether in n-hexane:

Size : 5 × 20 cm
Support : Glass
Layer Thickness : 0.25 mm

Pure product appears as a single homogeneous spot as spot 2 starting with fraction 16 until 21. The resulting TLC plates are illustrated in FIG. 1. These fractions are then analyzed using GLC, IR, NMR and Mass Spectral analyses which confirm the structure of the resulting product as being:

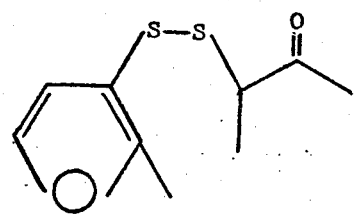

This material has a meaty, sweet, yeasty aroma and flavor with hydrolyzed vegetable protein-like and nutty nuances.

NMR analysis is as follows:

| SIGNAL | | INTERPRETATION | |
|---|---|---|---|
| 1.43 ppm | (d) | CH$_3$—C(S)—C=O | 3 H |
| 2.18 | (s) | CH$_3$—C=O | 3 H |
| 2.38 | (s) | (furan)—CH$_3$ | 3 H |
| 3.54 | (q) | HC—S, C=O | 1 H |
| 6.41 | (d) | (furan H) | 1 H |
| 7.26 | (d) | (furan H) | 1 H |

IR analysis is as follows: 725, 880, 930, 1080, 1120, 1190, 1220, 1350, 1365, 1380, 1435, 1510, 1700, 2920 cm⁻¹.

Mass Spectral Analysis is as follows:

| m/e | Relative Intensity |
|---|---|
| 43 | 75[2] |
| 45 | 15[6] |
| 51 | 10 |
| 59 | 23[5] |
| 81 | 12 |
| 113 | 100[1] |
| 114 | 44[4] |
| 145 | 12 |
| 173 | 13 |
| 216 | 63[3] |
| M232 | 0 |

EXAMPLE VI

The (2-methyl-3-furyl)(1-methyl-2-oxopropyl)disulfide prepared in Example V is dissolved in propylene glycol to provide a 0.1% solution. This solution in the amount of 0.9 g is added to 7.3 g of a soup base consisting of:

| Ingredient | Parts by Weight |
|---|---|
| Fine ground sodium chloride | 35.5 |
| Hydrolyzed vegetable protein | 27.5 |
| Monosodium glutamate | 18.0 |
| Sucrose | 11.0 |
| Beef fat | 5.5 |
| Sethness caramel color (powder B & C) | 2.7 |

The resulting beef broth flavor has a meaty, sweet yeasty aroma and taste with hydrolyzed vegetable protein-like and nutty nuances.

EXAMPLE VII

PREPARATION OF (2-METHYL-3-FURYL)(1-METHYL-2-OXOPROPYL) SULFIDE

Reaction:

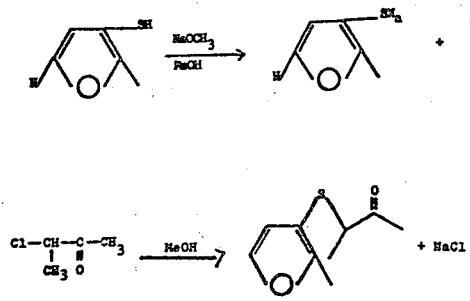

Into a 25 ml round bottom flask equipped with magnetic stirrer, thermometer and reflux condenser, a solution of 0.27 g (0.005 moles) of sodium methylate in 3 ml absolute methanol is added. 0.005 moles (0.57 g) of 2-methyl-3-furan thiol dissolved in 3 ml absolute methanol is then added slowly with stirring. The resulting yellow solution is allowed to stir for 10 minutes. 0.53 g (0.005 moles) of 3-chloro-2-butanone dissolved in 1 ml absolute methanol is then added dropwise over a 2 minute period. An exothermic reaction takes place with precipitation of sodium chloride indicating that the reaction is proceeding. During the reaction the temperature of the reaction mass is maintained at 25° – 35° C.

10 ml of water is then added to the reaction mass and the pH is adjusted to pH = 6 with 4% hydrochloric acid. 10 ml n-hexane is then added to the reaction mass and the resulting phases are separated. The aqueous phase is extracted with 6 ml of n-hexane and the hexane and organic phases are combined, washed with saturated sodium chloride, and dried over anhydrous sodium sulfate. The resulting solution is then concentrated in vacuo on a rotary evaporator to yield 0.76 g of a crude oil.

The desired product is isolated by GLC on an 8 foot × ¼ inch SE-30 column.

NMR, IR and Mass Spectral analyses give rise to the conclusion that the resulting material has the structure:

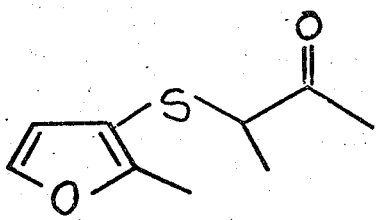

This material has a sweet, meaty, rubbery aroma with a cooked liver nuance and a sweet, cooked liver, hydrolyzed vegetable protein-like flavor with rubbery, meaty, pecan and mouth feel nuances.

NMR analysis is as follows:

| SIGNAL | | INTERPRETATION | |
|---|---|---|---|
| 1.32 ppm | (d) | CH₃—C(H)—C=O | 3 H |
| 2.32 | (s) | CH₃—C=O | |
| 2.32 | (s) | (furan ring with CH₃) | 6H |
| 3.46 | (q) | Me—C(H)(S—)—C=O | 1 H |
| 6.24 | (d) | (furan H) | 1 H |

| SIGNAL | INTERPRETATION | |
|---|---|---|
| 7.26 (d) |  | 1 H |

IR analysis is as follows: 730, 885, 935, 1060, 1085, 1125, 1155, 1190, 1225, 1350, 1370, 1385, 1440, 1510 1705, 2930, 2970 cm$^{-1}$.

Mass Spectral Analysis is as follows:

| m/e | Relative Intensity |
|---|---|
| 27 | 32[6] |
| 43 | 100[1] |
| 45 | 29 |
| 51 | 21 |
| 59 | 46[5] |
| 69 | 14 |
| 79 | 16 |
| 113 | 54[3] |
| 141 | 89[2] |
| M184 | 46[4] |

EXAMPLE VIII (2-methyl-3-furyl)(1-methyl-2-oxopropyl) sulfide prepared according to the process of Example VII is added to a 2% solution of Wyler's "Beef Flavored Instant Bouillon" (manufactured by Wyler Foods, Division of Borden, Inc., Chicago, Ill. U.S.A.).

(Ingredients: salt, hydrolyzed vegetable protein, malto dextrin, sugar beef fat, water, monosodium glutamate, flavorings, corn sugar, beef extract, caramel color, hydrogenated vegetable fat and U.S. certified food color)

at the rate of 1 ppm. The resulting beef flavor has a sweet, meaty aroma with a cooked liver nuance and a sweet, cooked liver, hydrolyzed vegetable protein-like flavor with meaty pecan, and "mouth-feel" nuances.

EXAMPLE IX

PREPARATION OF (1,3-DIETHYLACETONYL)(2,5-DIMETHYL-3-FURYL)SULFIDE

Reaction:

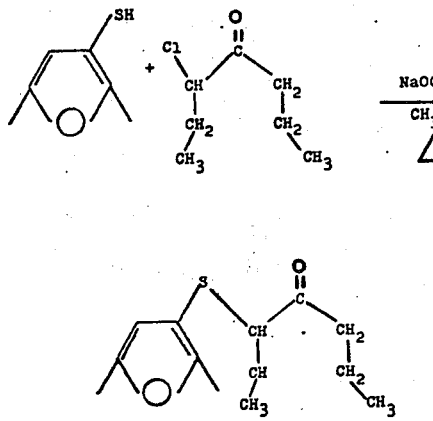

Into a 25 ml round bottom 3 neck flask equipped with magnetic stirrer, Y tube, nitrogen inlet, reflux condenser and thermometer is placed a solution of 0.27 g (0.005 moles) of sodium methoxide dissolved in 3 ml absolute methanol. The sodium methoxide solution is cooled using a water bath to 25° C. A solution of 0.64 g (0.005 moles) of 2,5-dimethyl-3-furan thiol in 3 ml of absolute methanol is then added to the sodium methoxide solution dropwise from a pipette while maintaining the temperature of the reaction mass between 22° C and 28° C. While maintaining the temperature of the reaction mass at 23° – 35° C, 3-chloro-4-heptanone (0.74 g; 0.005 moles) in 1 ml absolute methanol is added dropwise. The reaction mass is then stirred for a period of 1 hour while maintaining the temperature at 23° C. After this 1 hour period, 15 ml of water is added with stirring and the reaction mass temperature rises to 28° – 30° C. The reaction mass is cooled to 25° C using a water bath and now exists in an aqueous phase and an organic phase. The aqueous phase (pH=6) is extracted with two 6 ml portions of n-hexane; and the hexane extracts and organic phase are combined, washed with a 4 ml portion of saturated sodium chloride solution and then dried over anhydrous sodium sulfate. The resulting material is gravity filtered and concentrated on a rotary evaporator at 25° – 35° C and 15 mm Hg pressure, yielding a crude yellow oil weighing 1.2 g. The desired product is isolated by GLC trapping (8 foot × ¼ inch SE-30 Column), and NMR, IR and Mass Spectral analyses yield the information that this material has the structure:

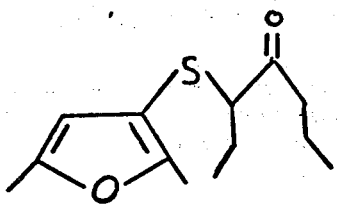

This material has a meaty, sweet and metallic aroma with a bloody nuance and a meaty, sweet and metallic flavor with a hydrolyzed vegetable protein-like and bloody nuance.

NMR analysis is as follows:

| SIGNAL | | INTERPRETATION | |
|---|---|---|---|
| 0.94 ppm | (t) | CH$_3$—C—C—C— (with C=O) | 6 H |
| 0.98 | (t) | CH$_3$—C—C—S— | |
| 1.64 | (m) | —CH$_2$ | 4 H |
| 2.22 | (s) | (dimethylfuryl ring, CH$_3$ and CH$_3$) | 6 H |
| 2.27 | (s) | | |
| 2.60 | (m) | —CH$_2$—C=O | 2 H |
| 3.20 | (t) | —S—C—C=O (with H) | 1 H |
| 5.82 | (s) | Furyl proton | 1 H |

IR analysis is as follows: 1060, 1220, 1360, 1375, 1430, 1450, 1565, 1700, 2870, 2920, 2960 cm$^{-1}$.

Mass Spectral analysis is as follows:

| m/e | Relative Intensity |
|---|---|
| 39 | 6 |
| 41 | 11[6] |
| 43 | 44[3] |
| 71 | 7 |
| 127 | 100[1] |
| 128 | 13[5] |
| 169 | 54[2] |
| 170 | 7 |
| M240 | 36[4] |
| 241 | 7 |

EXAMPLE X (1,3-diethylacetonyl) (2,5-dimethyl-3-furyl) sulfide prepared according to the process of Example IX is added to a 2% solution of Wyler's "Beef Flavored Instant Bouillon" (manufactured by Wyler Foods, Division of Borden, Inc., Chicago, Ill., U.S.A.).

(Ingredients: salt, hydrolyzed vegetable protein, malto dextrin, sugar, beef fat, water, monosodium glutamate, flavorings, corn sugar, beef extract, caramel color, hydrogenated vegetable fat and U.S. certified food color)

at the rate of 0.1 ppm. The use of (1,3-diethylacetonyl) (2,5-dimethyl-3-furyl) sulfide adds a meaty, sweet aroma with a bloody nuance; and a meaty, sweet flavor with hydrolyzed vegetable protein-like and bloody nuances to the beef broth.

EXAMPLE XI (CAMPHOR-3-YL)(2-METHYL-3-FURYL)SULFIDE

Reaction:

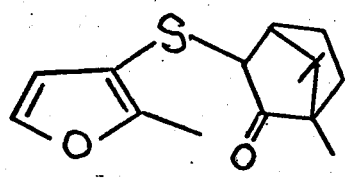

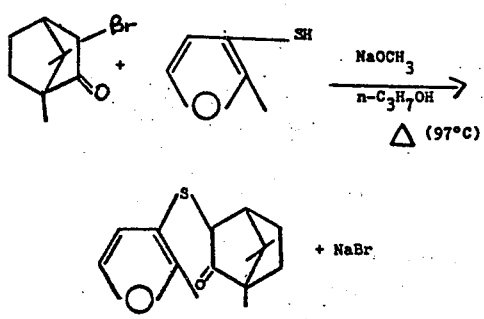

Into a 25 ml 3 neck round bottom flask equipped with magnetic stirrer, reflux condenser, Y-tube, thermometer, calcium chloride drying tube, heating mantle and nitrogen inlet tube, a solution of 0.27 g (0.005 moles) of sodium methoxide in n-propanol is placed. With stirring, 0.57 g (0.005 moles) of 2-methyl-3-furan thiol in 3 ml of n-propanol is added to the sodium methoxide solution thus yielding a yellow solution. While maintaining the temperature at 25° C, 1.16 g (0.005 moles) of d-3-bromo-camphor in 8 ml of propanol is added to the reaction mass. The reaction mass is then heated to reflux temperature (97° C) and refluxing is continued for a period of 6 hours. At the end of the 6 hour reflux period, the reaction mass is cooled to 33° C and transferred to a rotary evaporator and concentrated to a dark brown solution having a volume of approximately 8 ml. Hexane is added to the reaction mass followed by water thereby creating a two phase system. The phases are separated and the aqueous phase is extracted with hexane. The hexane extracts are combined and washed with saturated sodium chloride; dried over anhydrous sodium sulfate and concentrated to a crude brown oil. The aqueous phase is neutralized to a pH of 7 and extracted with diethylether. The extract is washed with sodium chloride and dried and concentrated to a brown oil. The oils are combined (from the hexane and from the diethylether extracts) and the desired product is isolated by GLC trapping (8 foot × ¼ inch SE-30 Column). NMR, IR and Mass Spectral analyses confirm that the product has the structure:

This material has a sweet, meaty, crispy aroma and a sweet, meaty, roasted flavor.

NMR analysis is as follows:

| SIGNAL | | INTERPRETATION | |
|---|---|---|---|
| 0.86 ppm | (s) | quaternary | |
| 0.94 | (s) | methyl protons of camphor | 9 H |
| 1.02 | (s) | | |
| 2.22–1.32 | (m) | camphor methylene and methine protons | 5 H |
| 2.40 | (s) | furyl methyl protons | 3 H |
| 3.60 | (d) | HC—C— ‖ O | 1 H |
| 6.46 | (d) | H$_4$ of furan | 1 H |
| 7.28 | (d) | H$_5$ of furan | 1 H |

IR analysis is as follows: 725, 880, 1030, 1080, 1120, 1215, 1365, 1385 1440, 1505, 1735, 2860, 2920, 2950 cm$^{-1}$.

Mass Spectral analysis is as follows:

| m/e | Relative Intensity |
|---|---|
| 39 | 20 |
| 41 | 49[4] |
| 43 | 41[6] |
| 55 | 31 |
| 81 | 26 |
| 83 | 22 |
| 113 | 45[5] |
| 123 | 50[3] |
| 153 | 100[1] |
| M264 | 97[2] |

EXAMPLE XII (Camphor-3-yl)(2-methyl-3-furyl) sulfide prepared according to the process of Example XI is added to a 2% aqueous solution of Wyler's "Beef Flavored Instant Bouillon" (manufactured by Wyler Foods, Division of Borden, Inc., Chicago, Ill. U.S.A.).

(Ingredients: salt, hydrolyzed vegetable protein, malto dextrin, sugar, beef fat, water, monosodium glutamate, "flavorings", corn sugar, beef extract, caramel color, hydrogenated vegetable fat, U.S. certified food color)

at the rate of 1 ppm. The resulting beef flavor has a sweet, meaty crispy aroma with intense sweet, roasted flavor notes.

EXAMPLE XIII

PREPARATION OF (2-METHYL-3-FURYL)(1,1,3,3-TETRAMETHYLACETONYL)SULFIDE

Reactions:

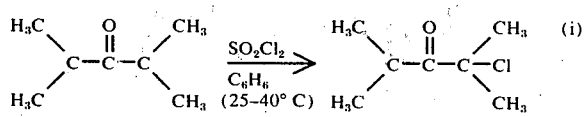

Reaction:

(ii)

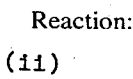

+

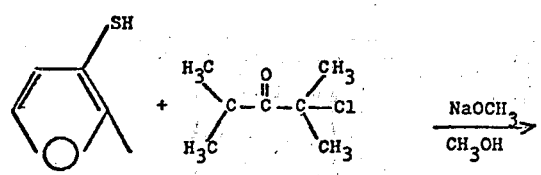

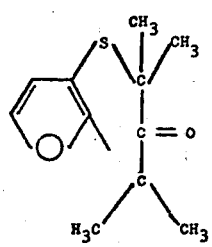

Into a 100 ml 3 neck round bottom flask equipped with magnetic stirrer, thermometer, reflux condenser, 50 ml addition funnel, water bath and gas outlet tube attached to water aspirator vacuum (at top of condenser) is placed 25.7 g (0.225 moles) of di-isopropyl ketone. Over a period of 20 minutes a solution of 20.3 g (0.15 moles) of SO₂CL₂ (sulfuryl chloride) in 12 ml of benzene is added to the di-isopropyl ketone. External cooling is applied as a result of the fact that the reaction is exothermic. After a 40 minute addition period, the reaction mass is stirred continuously while maintaining the temperature at 25° C. The reaction mass is then placed on a rotary evaporator for ½ hour, thus yielding 30 g of a water-white mixture. The reaction product is placed in a 100 ml round bottom 3 neck flask equipped with a 15 cm Vigreux column, magnetic stirrer, reflux condenser and heating mantle. The resulting material is fractionated yielding, 2,4-dimethyl-2-chloro-pentanone-3 having the structure:

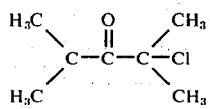

as confirmed by NMR, IR and Mass Spectral analyses.

Into a 25 ml round bottom 3 neck flask equipped with magnetic stirrer, Y tube, nitrogen inlet, reflux condenser, thermometer and heating mantle, is added 0.57 g (0.005 moles) 2-methyl-3-furan thiol in 3 ml absolute methanol and a solution of 0.27 g (0.005 moles) sodium methoxide in 3 ml of absolute methanol. After 10 minutes stirring, 0.74 g (0.005 moles) 2-chloro-2,4-dimethyl-3-pentanone in 1 ml absolute methanol is added slowly. The reaction mass is then warmed to 35° C using a hot water bath and while maintaining the temperature of the reaction mass at 35° C it is placed under a nitrogen blanket. The reaction mass is then heated to reflux (65°-66° C) and refluxed for a period of 1 hour. At the end of the 1 hour reflux period, the reaction mass is allowed to cool and is worked up by adding thereto 10 ml of water. The reaction mass, being at a basic pH (9–10), is acidified with dilute HCl bringing the pH down to 6. N-Hexane is added to the reaction mass giving rise to two phases; an aqueous phase and an organic phase. The aqueous phase is extracted with 2 × 10 ml of hexane. The hexane extracts are separated, combined, washed with saturated sodium chloride solution and then dried over anhydrous sodium sulfate. The resulting solution is then concentrated to a weight of 1.02 g and the desired compound is isolated using GLC apparatus (conditions: SE-30 Column, 8 foot × ¼ inch). NMR, IR and Mass Spectral analyses confirm that the structure of the resulting material is:

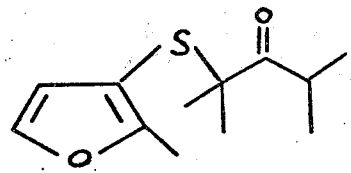

This material has a meaty, sulfury aroma, and a meaty, roast onion and sulfury flavor with a green note. It also has a garlic and alliaceous nuance. NMR analysis is as follows:

| SIGNAL | | INTERPRETATION | |
|---|---|---|---|
| 1.16 ppm | (d) | CH₃\C—C\ /CH₃ | 6 H |
| 1.42 | (s) | H₃C\C/ S— \C=O / H₃C | 6 H |
| 2.34 | (s) | furyl methyl protons | 3 H |

| SIGNAL | | INTERPRETATION | |
|---|---|---|---|
| 3.38 | (m) | $\underset{HC-C-}{\overset{O}{\parallel}}$ | 1 H |
| 6.18 | (d) | $H_4$ of furan | 1 H |
| 7.26 | (d) | $H_5$ of furan | 1 H |

IR analysis is as follows 730, 990, 1030, 1085, 1220, 1360, 1380, 1465, 1515, 1695, 2930, 2970 cm$^{-1}$.

Mass Spectral analysis is as follows:

| m/e | Relative Intensity |
|---|---|
| 27 | 8 |
| 41 | 21[3] |
| 43 | 39[2] |
| 59 | 10 |
| 93 | 10[6] |
| 113 | 16[5] |
| 114 | 8 |
| 155 | 100[1] |
| 156 | 8 |
| M226 | 18[4] |

EXAMPLE XIV (2-methyl-3-furyl)(1,1,3,3-tetramethylacetonyl) sulfide prepared according to the process of Example XIII is added to a 2% solution of Wyler's "Beef Flavored Instant Bouillon" (manufactured by Wyler Foods, Division of Borden, Inc., Chicago, Ill. U.S.A.)

(Ingredients: salt, hydrolyzed vegetable protein, malto dextrin, sugar, beef fat, water, monosodium glutamate, flavorings, corn sugar, beef extract, caramel color, hydrogenated vegetable fat, U.S. certified food color)

at the rate of 0.2 ppm. This chemical adds a natural meaty, sulfury aroma and meaty, roast onion and sulfury taste effect with a green, garlic and alliaceous nuances to the beef broth.

IN THE DRAWINGS:

FIG. 14 is the NMR spectrum for the product of Example XIII, wherein (2-methyl-3-furyl)(1,1,3,3-tetramethylacetonyl)sulfide is produced.

FIG. 15 is the IR spectrum for the product of Example XIII wherein (2-methyl-3-furyl)(1,1,3,3-tetramethylacetonyl)sulfide is produced.

Figure 1:
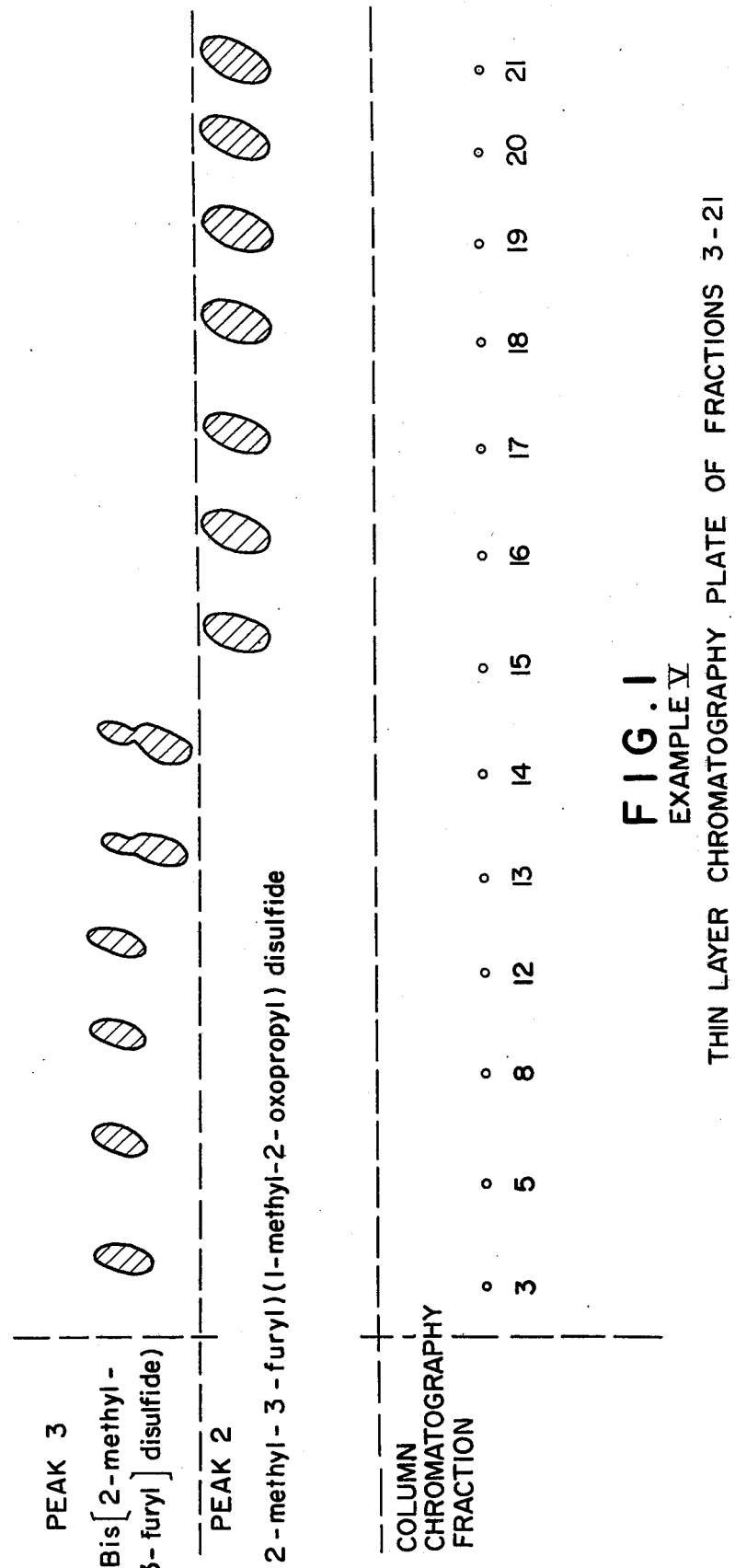
FIG. 1 is a drawing of the thin layer chromatography plates described in Example V, wherein (2-methyl-3-furyl)(1-methyl-2-oxopropyl)disulfide is produced.
Figure 2:
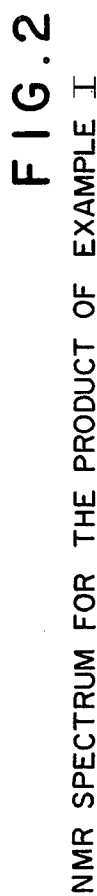
FIG. 2 is the NMR spectrum for the product of Example I, wherein (1,3-diethylacetonyl) (2-methyl-3-furyl)sulfide is produced.
Figure 3:
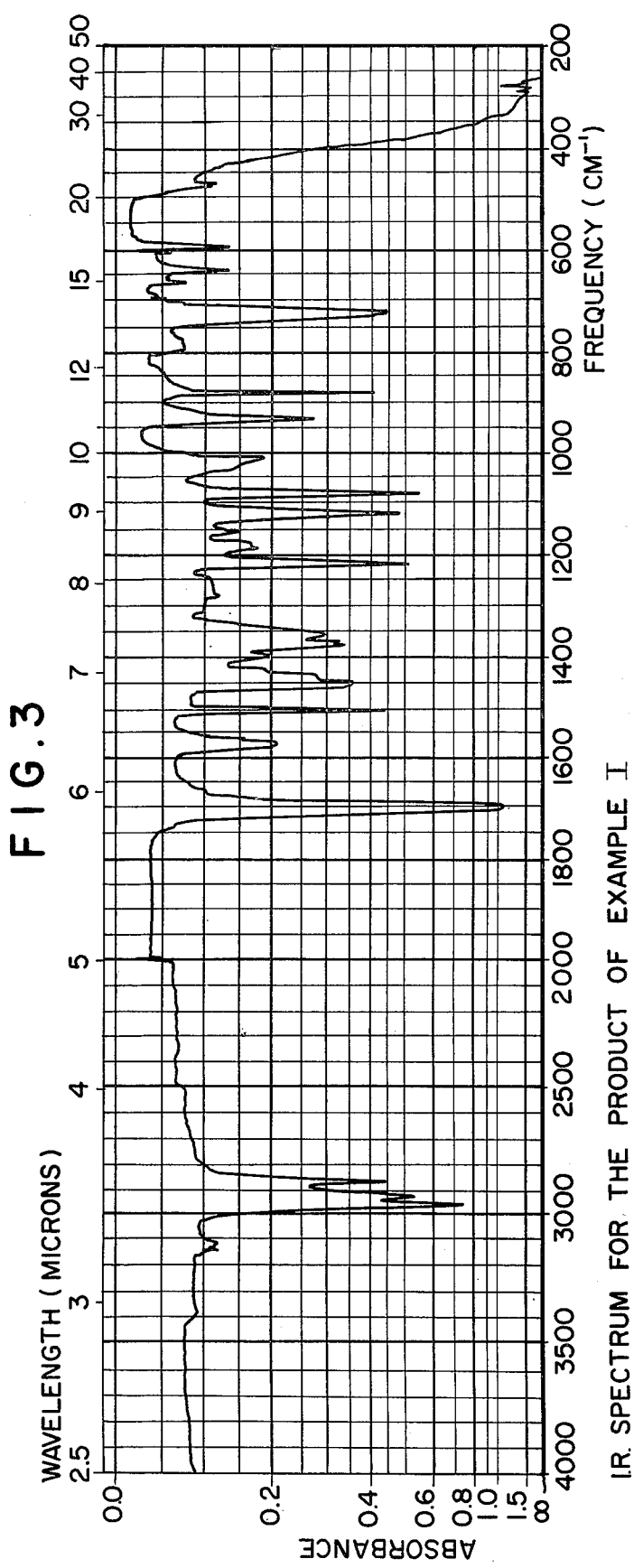
FIG. 3 is the IR spectrum for the product of Example I, wherein (1,3-diethylacetonyl)(2-methyl-3-furyl)sulfide is produced.
Figure 4:
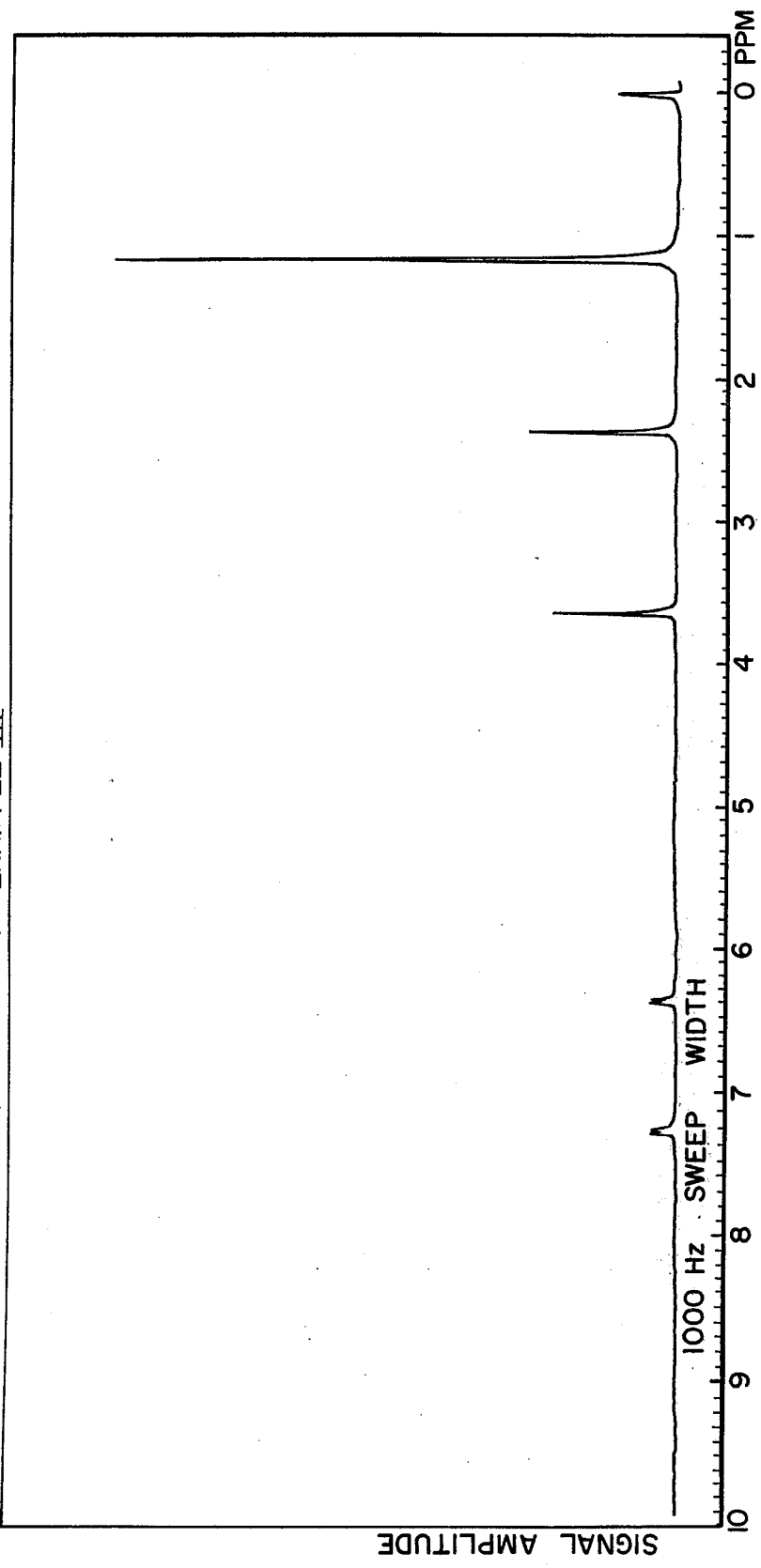
FIG. 4 is the NMR spectrum for the product of Example III, wherein (2-methyl-3-furyl)(3,3,3-trimethylacetonyl)sulfide is produced.
Figure 5:
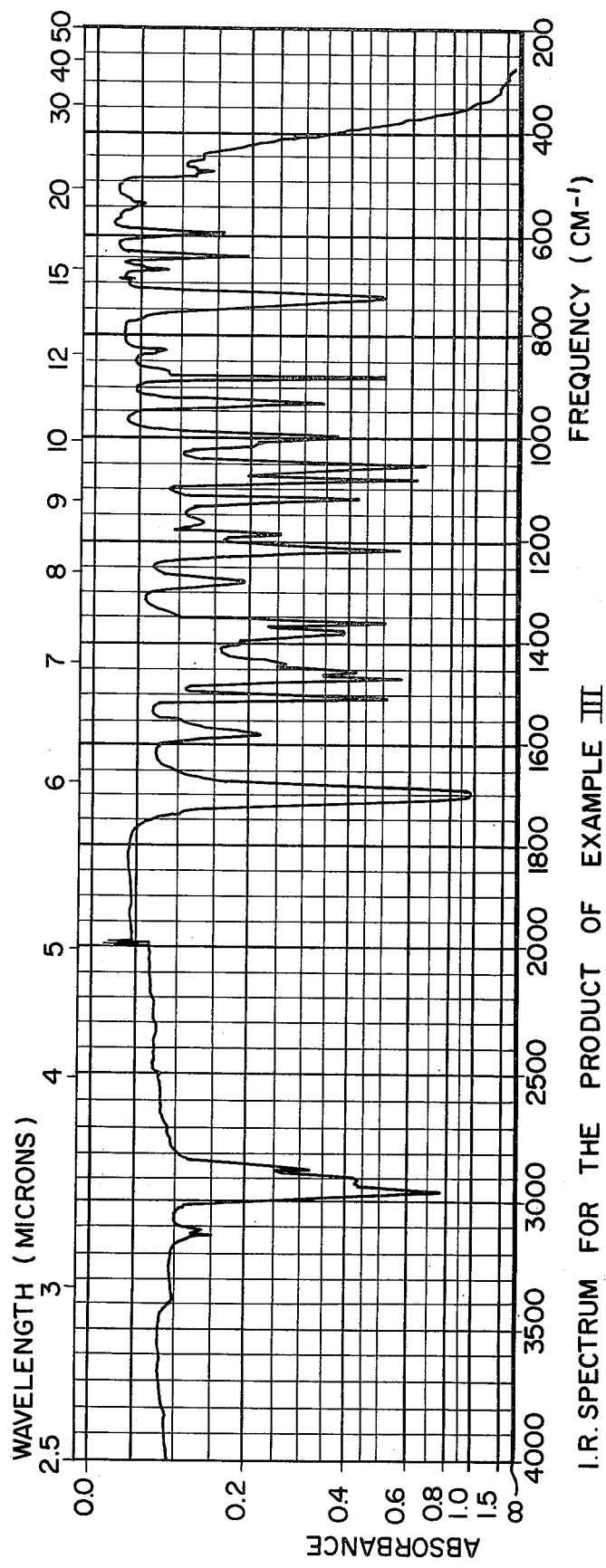
FIG. 5 is the IR spectrum for the product of Example III, wherein (2-methyl-3-furyl)(3,3,3-trimethylacetonyl)sulfide is produced.
Figure 6:
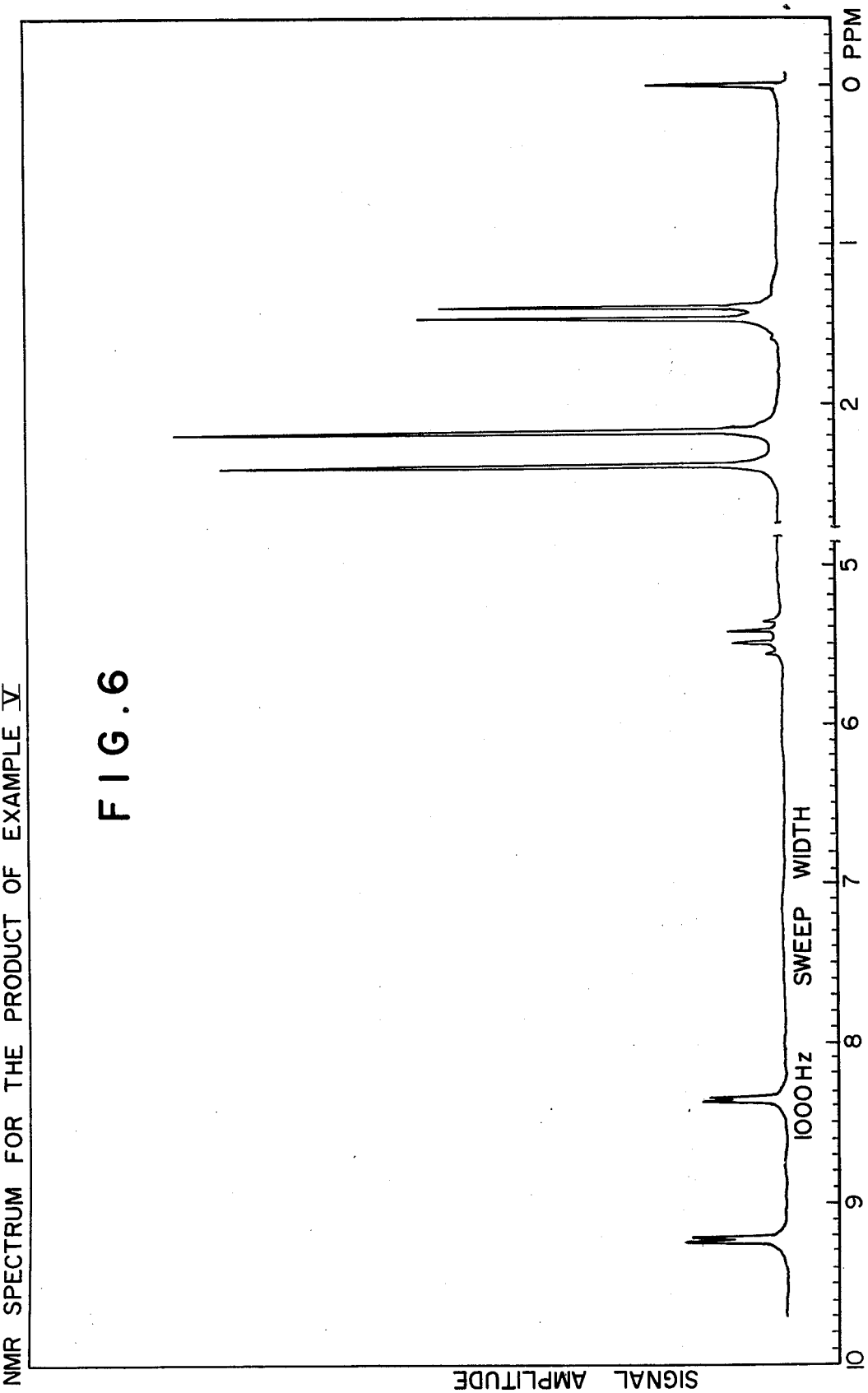
FIG. 6 is the NMR spectrum for the product of Example V, wherein (2-methyl-3-furyl)(1-methyl-2-oxopropyl)disulfide is produced.
Figure 7:
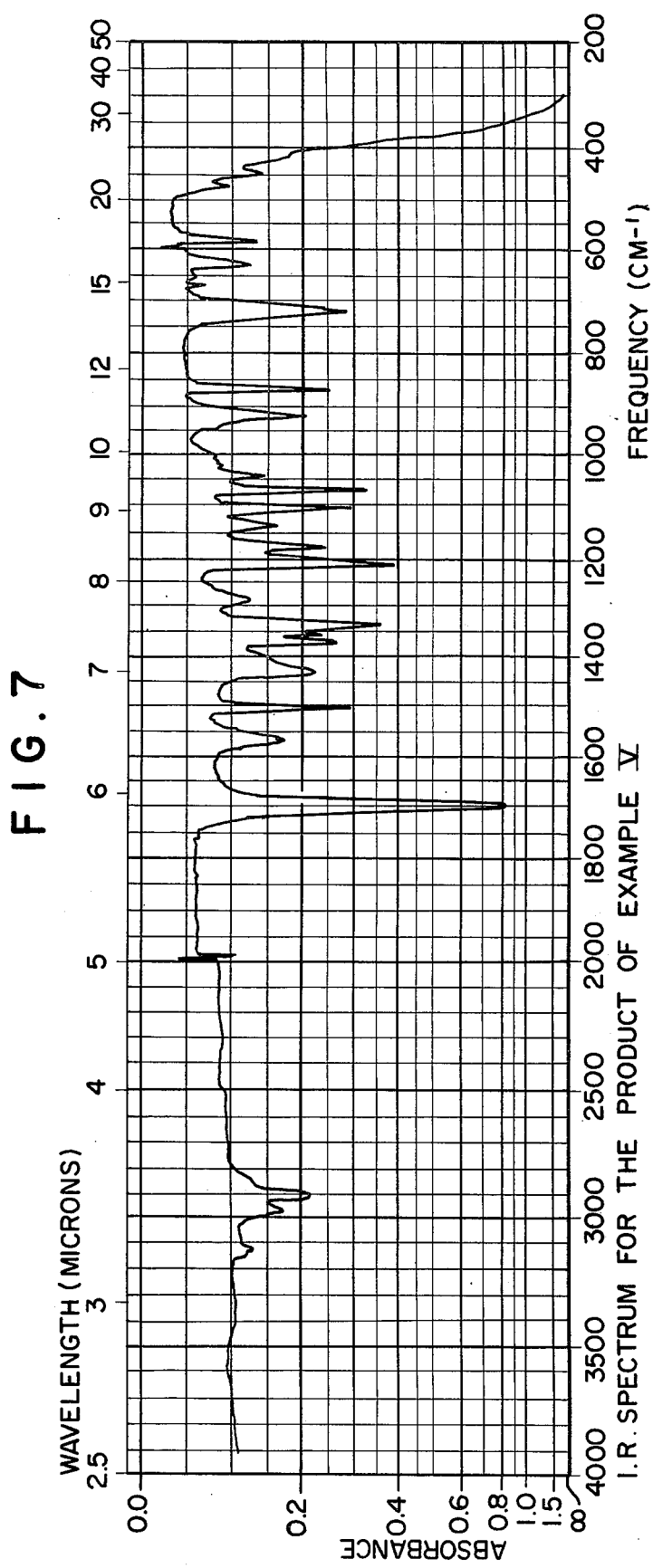
FIG. 7 is the IR spectrum for the product of Example V, wherein (2-methyl-3-furyl)(1-methyl-2-oxopropyl)disulfide is produced.
Figure 8:
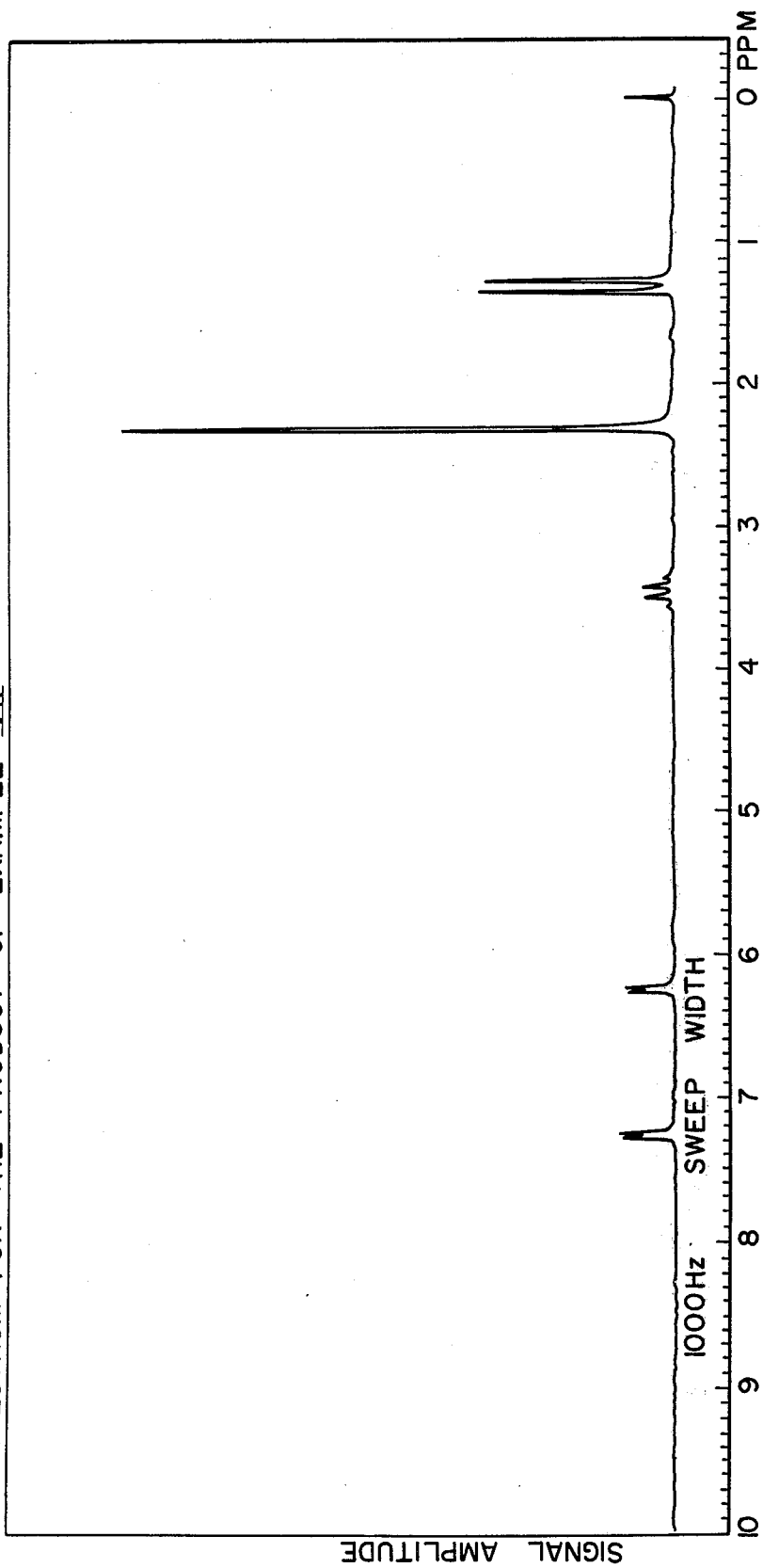
FIG. 8 is the NMR spectrum for the product of Example VII, wherein (2-methyl-3-furyl)(1-methyl-2-oxopropyl)sulfide is produced.
Figure 9:
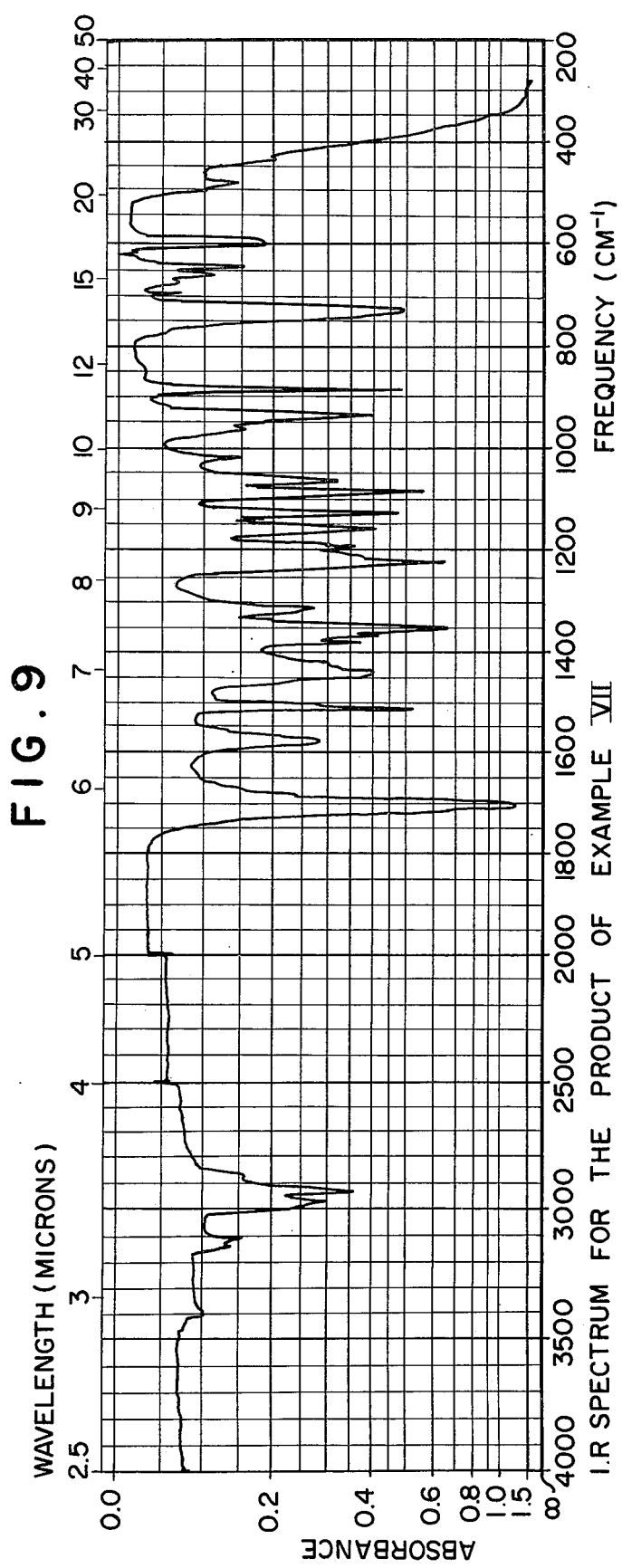
FIG. 9 is the IR spectrum for the product of Example VII, wherein (2-methyl-3-furyl)(1-methyl-2-oxopropyl)sulfide is produced.
Figure 10:
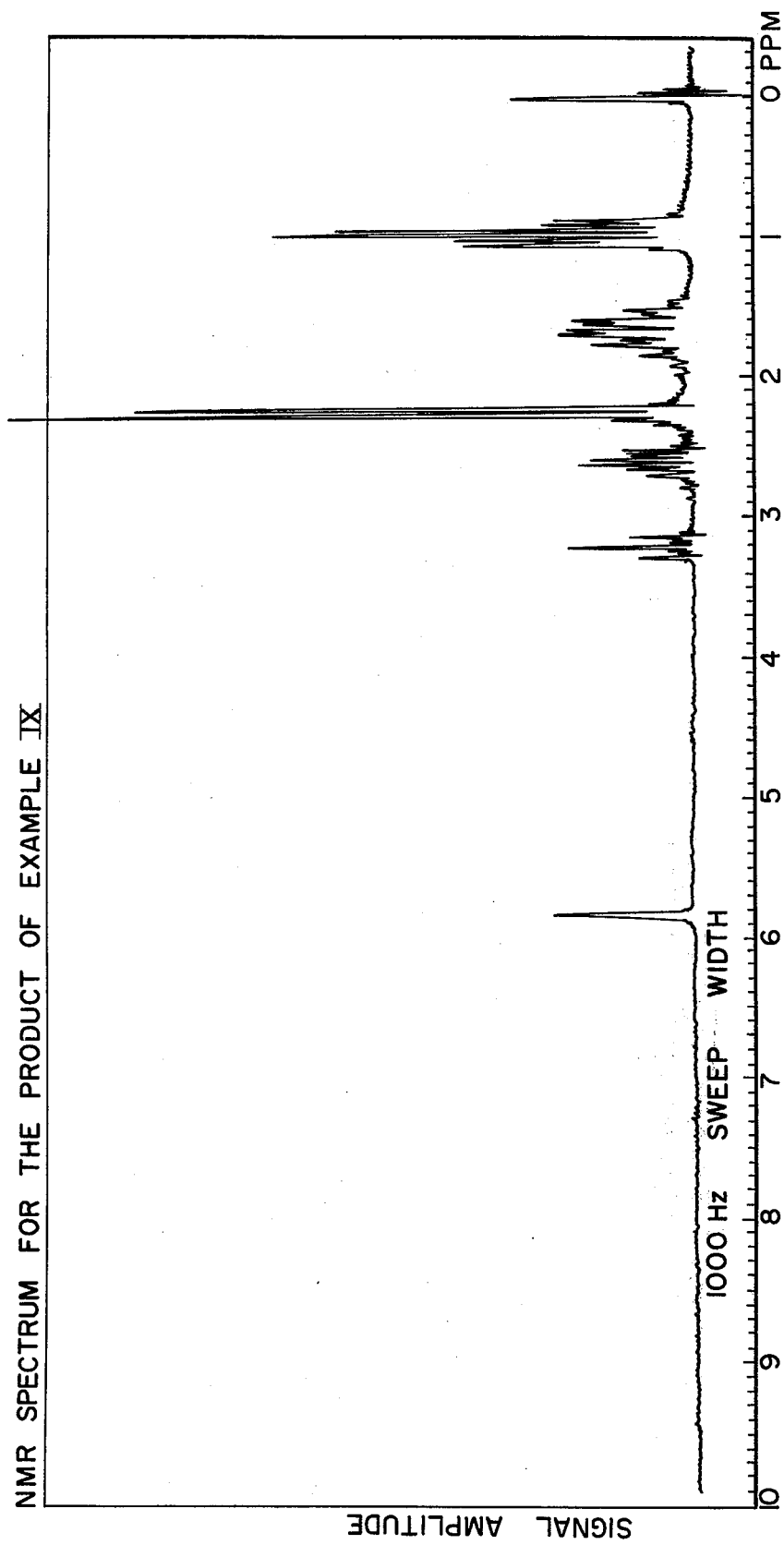
FIG. 10 is the NMR spectrum for the product of Example IX, wherein (1,3-diethylacetonyl)(2,5-dimethyl-3-furyl)sulfide is produced.
Figure 11:
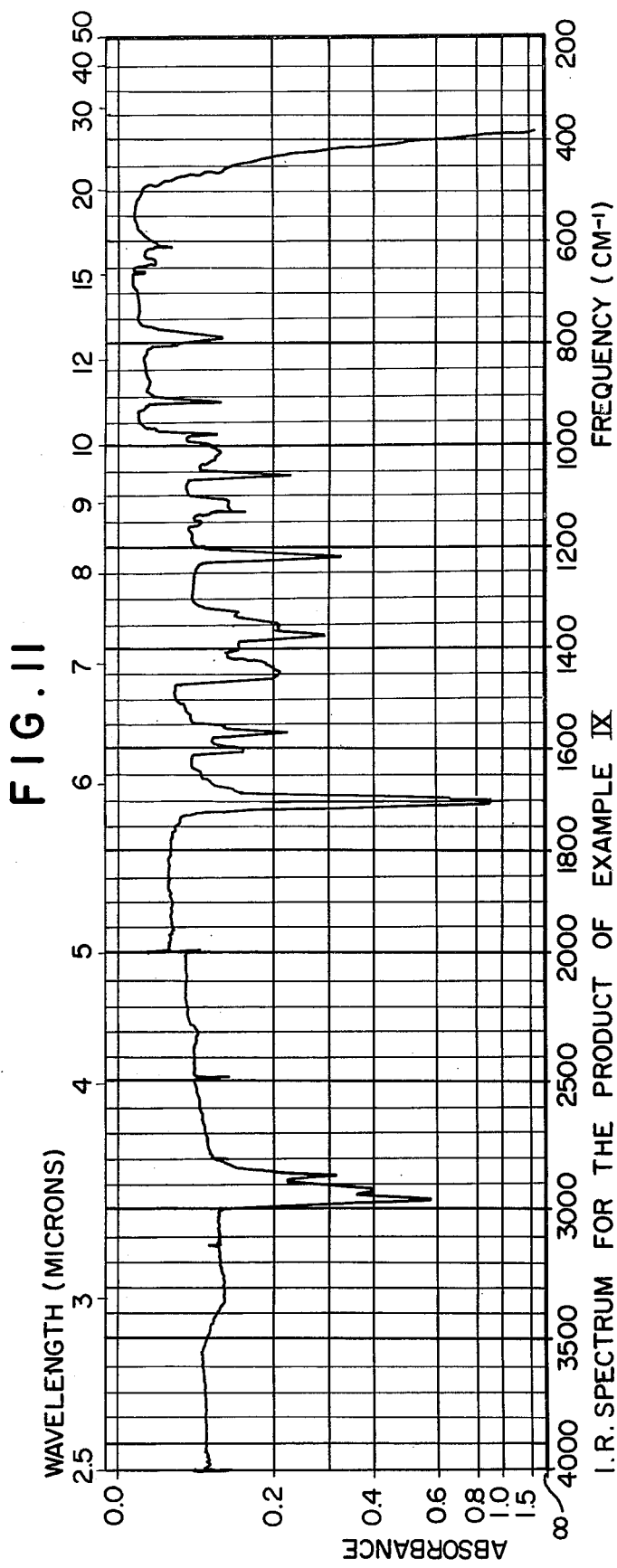
FIG. 11 is the IR spectrum for the product of Example IX, wherein (1,3-diethylacetonyl)(2,5-dimethyl-3-furyl)sulfide is produced.
Figure 12:
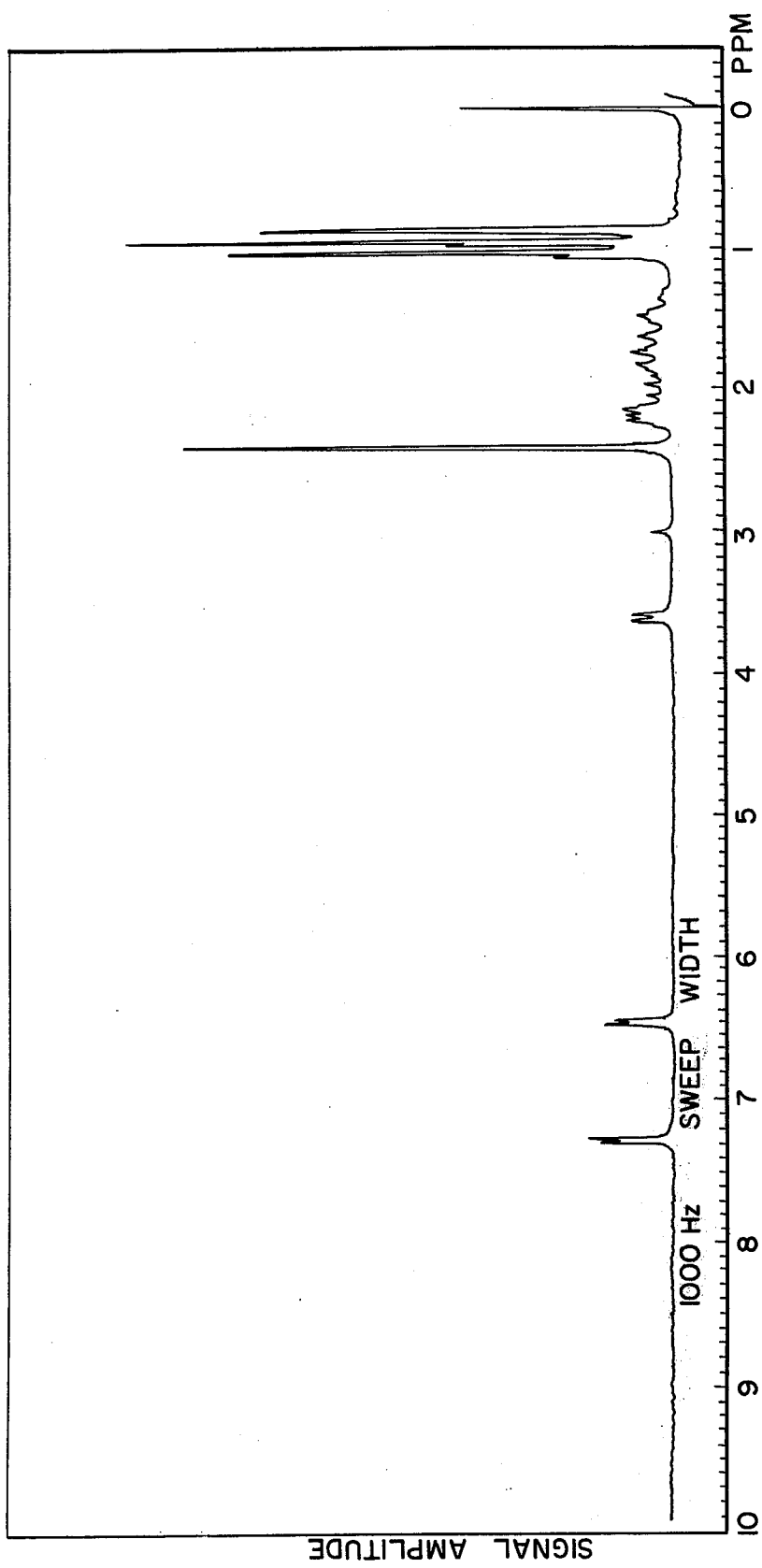
FIG. 12 is the NMR spectrum for the product of Example XI, wherein (camphor-3-yl)(2-methyl-3-furyl)sulfide is produced.
Figure 13:
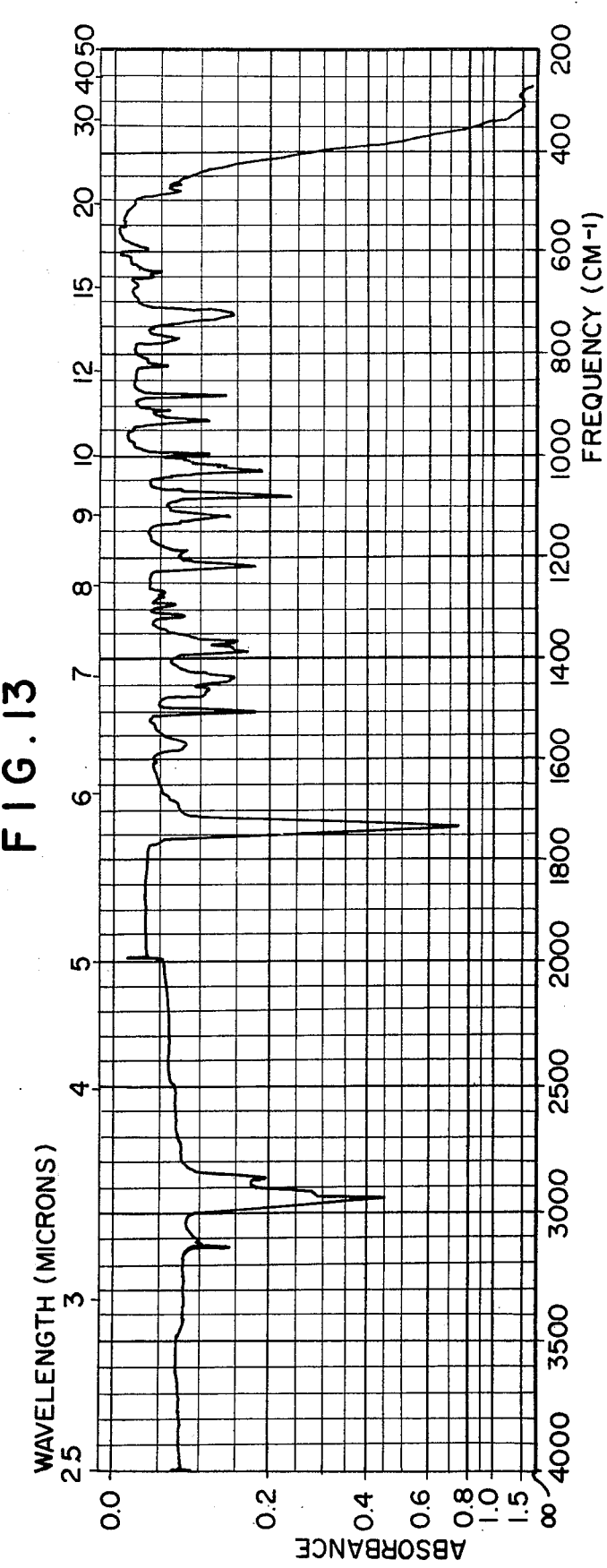
FIG. 13 is the IR spectrum for the product of Example XI, wherein (camphor-3-yl)(2-methyl-3-furyl)sulfide is produced.

What is claimed is:

1. A 3-furyl beta-oxoalkyl sulfide having the structure:

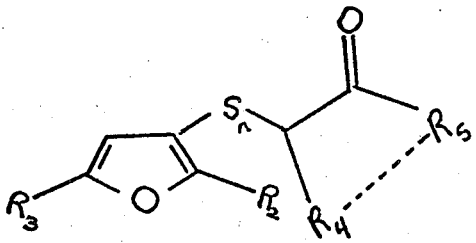

wherein $n$ is 1 or 2; $R_2$ and $R_3$ are each selected from the group consisting of methyl and hydrogen, at least one of $R_2$ and $R_3$ being methyl; and $R_4$ and $R_5$ taken separately, are each lower alkyl, or $R_4$ and $R_5$ taken together complete a cycloalkyl ring, or bicycloalkyl ring.

2. The 3-furyl beta-oxoalkyl sulfide compound of claim 1 wherein $R_2$ is methyl, $R_3$ is hydrogen, $R_4$ and $R_5$ are each lower alkyl and $n$ is one.

3. The 3-furyl beta-oxoalkyl sulfide compound of claim 1 having the structure:

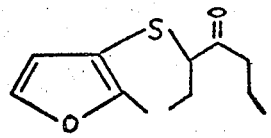

4. The 3-furyl beta-oxoalkyl sulfide compound of claim 1 having the structure:

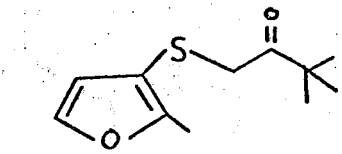

5. The 3-furyl beta-oxalkyl sulfide compound of claim 1 having the structure:

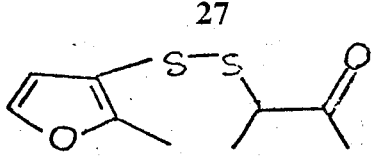

6. The 3-furyl beta-oxoalkyl sulfide compond of claim 1 having the structure:

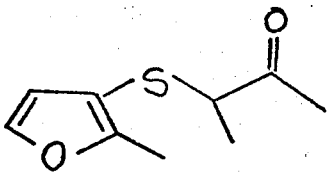

7. The 3-furyl beta-oxoalkyl sulfide compound of claim 1 having the structure:

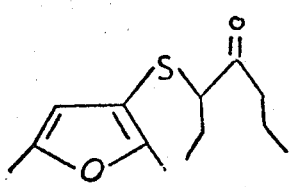

8. The 3-furyl beta-oxoalkyl sulfide compound of claim 1 having the structure:

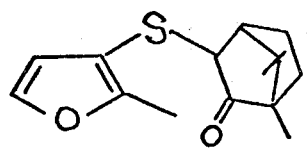

9. The 3-furyl beta-oxoalkyl sulfide compound of claim 1 having the structure:

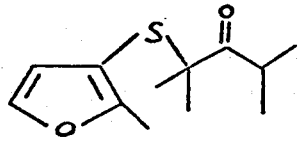

10. A process for augmenting or enhancing the meaty flavor of a foodstuff comprising the step of adding to said foodstuff from about 0.005 ppm up to about 250 ppm of a 3-furyl beta oxoalkyl sulfide compound having the structure:

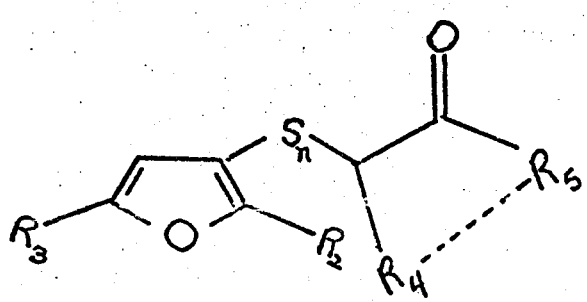

wherein $n$ is one or two; $R_2$ and $R_3$ are each selected from the group consisting of methyl and hydrogen, at least one of $R_2$ and $R_3$ being methyl; and $R_4$ and $R_5$ taken separately, are each lower alkyl, or $R_4$ and $R_5$ taken together complete a cycloalkyl or bicycloalkyl ring.

11. The process of claim 10, wherein the structure of the 3-furyl beta-oxoalkyl sulfide compound is:

12. The process of claim 10, wherein the structure of the 3-furyl beta-oxoalkyl sulfide compound is:

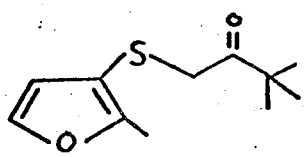

13. The process of claim 10, wherein the structure of the 3-furyl beta-oxoalkyl sulfide compound is:

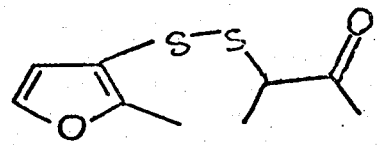

14. The process of claim 10, wherein the structure of the 3-furyl beta-oxoalkyl sulfide compound is:

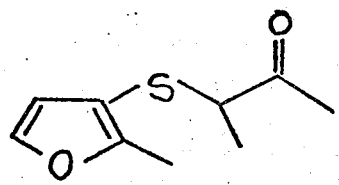

15. The process of claim 10, wherein the structure of the 3-furyl beta-oxoalkyl sulfide compound is:

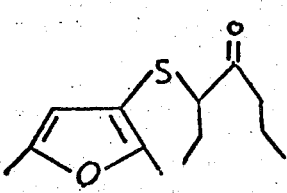

16. The process of claim 10, wherein the structure of the 3-furyl beta-oxoalkyl sulfide compound is:

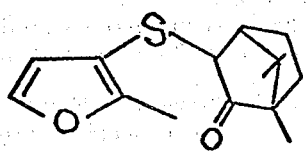

17. The process of claim 10, wherein the structure of the 3-furyl beta-oxoalkyl sulfide compound is:

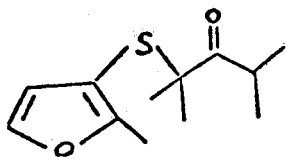

18. A flavoring composition for augmenting or enhancing the meaty flavor of a foodstuff comprising (i) from 0.5 ppm up to 90% of a 3-furyl beta-oxoalkyl sulfide having the structure:

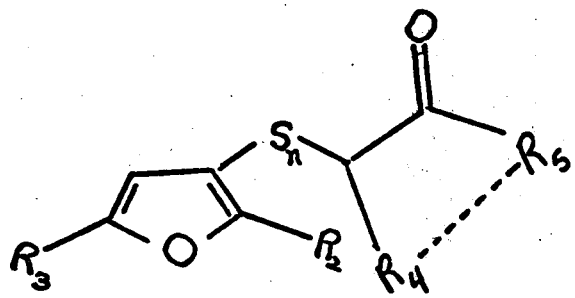

wherein $n$ is one or two; $R_2$ and $R_3$ are each selected from the group consisting of methyl and hydrogen, at least one of $R_2$ and $R_3$ being methyl; and $R_4$ and $R_5$ tkaen separately are each lower alkyl or $R_4$ and $R_5$ taken together, complete a cycloalkyl ring or a bicycloalkyl ring. (ii) the remainder of said composition being at least one flavoring adjuvant selected from the group consisting of:
- 4-Mercapto-2-butanone;
- 3-Mercapto-2-pentanone;
- 1-Mercapto-2-propanone;
- Benzaldehyde;
- Furfural;
- Furfural alcohol;
- 2-Mercapto propionic acid;
- Alkyl pyrazine;
- Methyl pyrazine;
- 2-Ethyl-3-methyl pyrazine;
- Tetramethyl pyrazine;
- Polysulfides;
- Dipropyl disulfide;
- Methyl benzyl disulfide;
- Alkyl thiophenes;
- 2-Butyl thiophene;
- 2,3-Dimethyl thiophene;
- 5-Methyl furfural;
- Acetyl furan;
- 2,4-Decadienal;
- Guiacol;
- Phenyl acetaldehyde;
- δ-Decalactone;
- d-Limonene;
- Acetoin;
- Amyl acetate;
- Maltol;
- Ethyl butyrate;
- Levulinic acid;
- Piperonal;
- Ethyl acetate;
- n-Octanol;
- n-Pentanal;
- Hexanal;
- Diacetyl;
- Monosodium glutamate;
- Sulfur-containing amino acids;
- Cysteine;
- Hydrolyzed vegetable protein;
- 2-Methylfuran-3-thiol;
- 2-Methyldihydrofuran-3-thiol;
- 2,5-Dimethylfuran-3-thiol;
- Hydrolyzed fish protein; and
- Tetramethyl pyrozine.

19. The flavor composition of claim 18, wherein the structure of the 3-furyl betaoxoalkyl sulfide is:

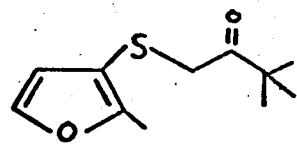

20. The flavor composition of claim 18, wherein the structure of the 3-furyl betaoxoalkyl sulfide is:

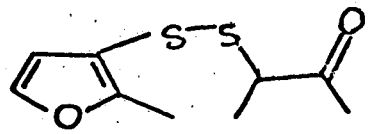

21. The flavor composition of claim 18, wherein the structure of the 3-furyl betaoxoalkyl sulfide is:

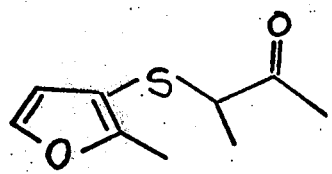

22. The flavor composition of claim 18, wherein the structure of the 3-furyl betaoxoalkyl sulfide is:

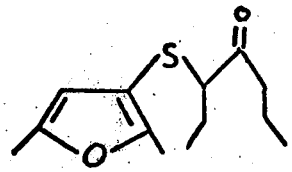

23. The flavor composition of claim 18, wherein the structure of the 3-furyl betaoxoalkyl sulfide is:

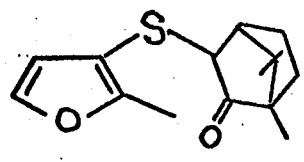

24. The flavor composition of claim 18, wherein the structure of the 3-furyl betaoxoalkyl sulfide is:

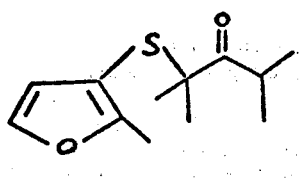

25. The process of claim 10 wherein the quantity range of said 3-furyl betaoxoalkyl sulfide in said foodstuff is from 0.01 ppm up to 100 ppm.

26. The flavor composition of claim 18 wherein the quantity range of 3-furyl betaoxoalkyl sulfide is from 1 ppm up to 0.1 percent.

27. The composition of claim 18 further including a carrier.

* * * * *